(12) United States Patent
Fukumoto et al.

(10) Patent No.: US 6,525,066 B2
(45) Date of Patent: Feb. 25, 2003

(54) 4-OXOQUINOLIZINE ANTIMICROBIAL HAVING 2-PYRIDONE SKELETON AS PARTIAL STRUCTURE

(75) Inventors: Ryoichi Fukumoto, Hachiouji (JP); Hiroyuki Kusakabe, Isumi-Gun (JP); Chong Chu, Oota-Ku (JP); Hiroaki Kimura, Arakawa-Ku (JP); Satoshi Yanagihara, Kawasaki (JP); Masatoshi Kato, Sagamihara (JP); Chisato Hirosawa, Tokyo (JP); Seiji Ishiduka, Hachioji (JP); Fusae Shizume, Tokyo (JP)

(73) Assignee: SATO Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/124,485

(22) Filed: Apr. 18, 2002

(65) Prior Publication Data
US 2002/0173517 A1 Nov. 21, 2002

Related U.S. Application Data

(63) Continuation of application No. PCT/JP00/07256, filed on Oct. 19, 2000.

(30) Foreign Application Priority Data

Oct. 19, 1999 (JP) ............................................. 11-296383

(51) Int. Cl.[7] ..................... A61K 31/435; C07D 471/04
(52) U.S. Cl. ........................................ 514/306; 546/138
(58) Field of Search ........................... 546/138; 514/306

(56) References Cited

FOREIGN PATENT DOCUMENTS

| EP | 0 775 702 | 5/1997 |
|---|---|---|
| JP | 09-136886 | 5/1997 |

OTHER PUBLICATIONS

Ma et al., Synthesis and Antimicrobial Activity of 4H–4–Oxoquinolizine Derivatives: Consequences of Structual Modification at the C–8 Position, pp. 4202–4213, 1999, J. Med. Chem., 42.

*Primary Examiner*—Bernard Dentz
(74) *Attorney, Agent, or Firm*—Nixon Peabody LLP; Donald R. Studebaker

(57) ABSTRACT

A compound represented by the following Formula (I) or a pharmaceutically acceptable salt thereof:

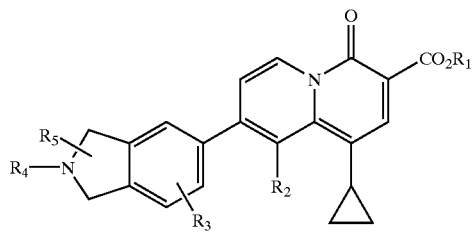

wherein $R_1$ represents a hydrogen atom or a carboxyl-protecting group, $R_2$ represents a hydrogen atom, a halogen atom, a lower alkyl group, a lower alkoxy group or a hydroxyl group, $R_3$ represents a hydrogen atom, a halogen atom, a lower alkyl group, a lower alkoxy group, a lower alkylthio group, a nitro group, a cyano group, a hydroxyl group or an amino group;

$R_4$ represents a hydrogen atom, an amino-protecting group, an alkyl group or a cycloalkyl group, and $R_5$ represents a hydrogen atom, a halogen atom, an alkyl group, an alkenyl group, a cycloalkyl group, an aryl group, an alkoxy group, an alkylthio group, a hydroxyl group, an imino group or an amino group.

14 Claims, 5 Drawing Sheets

Reaction Scheme 1

Reaction Scheme 2

Reaction Scheme 3

Reaction Scheme 4

Reaction Scheme 5

4-OXOQUINOLIZINE ANTIMICROBIAL HAVING 2-PYRIDONE SKELETON AS PARTIAL STRUCTURE

This application is a continuation of international application number PCTJP00/07256, filed Oct. 19, 2000.

TECHNICAL FIELD

The present invention relates to a novel synthetic antimicrobial which exhibits strong antibacterial activities against Gram-positive, Gram-negative bacteria and anaerobic bacteria.

BACKGROUND TECHNOLOGY

Quinolone type synthetic antimicrobials have been widely used in the clinical field as an agent having an excellent antibacterial activity. However, compared to Cephalosporin and Penicillin type β-lactam antibiotics, Quinolone type synthetic antimicrobials have problems, for example, that they cause a lot of side effects concerning the central nervous system, that they cause critical side effects such as a spasm inducement, and that bacteria resistant due to such antimicrobials rapidly spread. Therefore, it has been desired that synthetic antibacterial agents be developed which are effective against the bacteria resistant to such an antimicrobial and have fewer side effects and a broad antibacterial spectrum.

In recent years, many studies on Quinolone type antimicrobials have been made since Norfloxacin, a Quinolone type compound including a fluorine at the 6-position, was developed. However, there are not many studies on 4-oxoquinolizine antimicrobials having a 2-pyridone skeleton as a partial structure has been made intensively.

Therefore, the present invention provides a 4-oxoquinolizine antimicrobial having new structure and strong antibacterial activities against Gram-positive, Gram-negative bacteria, and anaerobic bacteria.

DISCLOSURE OF INVENTION

The present inventors have conducted extensive research to provide an excellent antimicrobial, and found out that the compounds represented by the following Formula (I) has fewer side effects such as spasm inducement than the conventional antimicrobials and exhibits a strong antibacterial activity. The present invention has been completed on the basis of this finding.

Specifically, the present invention is related to a compound represented by the following Formula (I) or a pharmaceutically acceptable salt thereof:

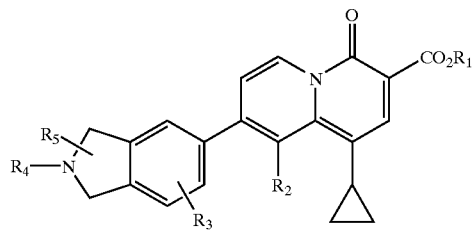

wherein
$R_1$ represents a hydrogen atom or a carboxyl-protecting group,
$R_2$ represents a hydrogen atom, a halogen atom, a lower alkyl group, a lower alkoxy group or a hydroxyl group,
$R_3$ represents a hydrogen atom, a halogen atom, a lower alkyl group, a lower alkoxy group, a lower alkylthio group, a nitro group, a cyano group, a hydroxyl group or an amino group;
$R_4$ represents a hydrogen atom, an amino-protecting group, an alkyl group or a cycloalkyl group, and
$R_5$ represents a hydrogen atom, a halogen atom, an alkyl group, an alkenyl group, a cycloalkyl group, an aryl group, an alkoxy group, an alkylthio group, a hydroxyl group, an imino group or an amino group.

EMBODIMENT FOR WORKING OF INVENTION

Figure 1:
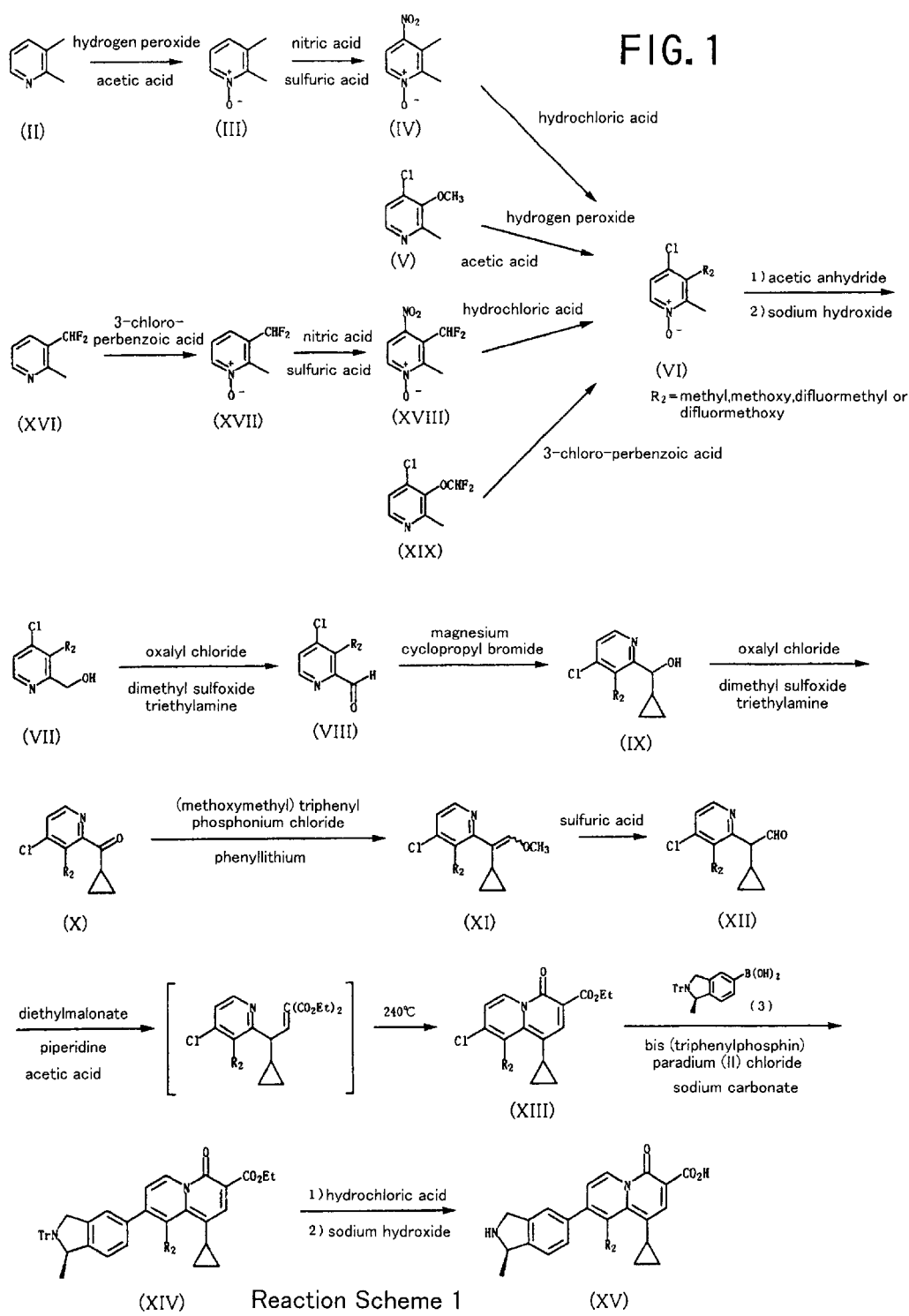
FIG. 1 shows Reaction Scheme 1.

The present invention will be explained in detail below.

In the present specification, unless otherwise specified, the following terms have the following meanings.

The term "alkyl group" means a saturated alkyl group having usually $C_{1-20}$, preferably $C_{1-15}$, and more preferably $C_{1-10}$ and may have a straight chain or branched chain. Particularly, the alkyl group includes lower and higher alkyl groups. The lower alkyl group includes an alkyl group whose carbon number is, for example, $C_{1-8}$, preferably about $C_{1-5}$.

The alkyl group includes a lower alkyl group, e.g., methyl, ethyl, n-propyl, isopropyl, n-butyl, isobutyl, sec-butyl, tert-butyl and pentyl, as well as an alkyl group such as a decyl, dodecyl, tridecyl and undecyl.

The term "alkenyl group" means a group having a double bond in the corresponding alkyl group. The alkenyl group includes a straight chain or branched chain alkenyl group.

The alkenyl group includes a straight chain or branched chain alkenyl group such as vinyl, allyl, propenyl, isopropenyl, butenyl, pentenyl, isopentenyl, hexenyl, octenyl, nonenyl and decenyl groups.

A cycloalkyl group is a cyclic alkyl group and includes cyclopropyl, cyclobutyl, cyclopentyl, cyclohexyl, cycloheptyl, cyclononyl, cyclodecyl and cyclododecyl groups.

An aryl group includes a phenyl and an anthracene group.

If necessary, the alkyl, alkenyl, cycloalkyl and aryl groups may have a substituent. Such a substituent includes halogen atom, hydroxyl, amino, cyano, isocyanate, epoxy, carboxyl and sulfonyl groups.

A halogen atom includes fluorine, chlorine, bromine and iodine atoms.

If necessary, the hydrogen atoms bound to the nitrogen atom of the amino or imino group may be substituted therefore. For example, such a substituent is preferably an alkyl group. Such an alkyl group includes a straight or branched alkyl group. Such an alkyl group may be selected from the groups as stated above.

A substituted amino group includes a monoalkylamino and a dialkylamino group. Such an alkyl group includes the alkyl group as stated above. Such a monoalkylamino group includes a methylamino, ethylamino, n-propylamino, isopropylamino, n-butylamino, isobutylamino, secbutylamino and tert-butylamino. If necessary, an alkyl group contained in the alkylamino group may have the substituent as stated above.

The dialkylamino group may have two different alkyl groups. Such a dialkylamino group includes dimethylamino, methylethylamino and diethylamino groups. Furthermore, if necessary, the alkyl group contained in the dialkylamino group may have the substituent as stated above.

Similarly, the alkylimino group includes methylimino, ethylimino, n-propylimino, isopropylimino, n-butylimino, isobutylimino, sec-butylimino and tert-butylimino groups.

An alkoxy group is a group containing the oxygen atom bound to an alkyl group. The alkyl group contained in the alkoxy group includes the alkyl groups as stated above. For example, a lower alkoxy group includes a straight or branched chain lower alkoxy group, such as methoxy, ethoxy, n-propoxy, isopropoxy, n-butoxy, isobutoxy, sec-butoxy, tert-butoxy and penthyloxy groups. Furthermore, if necessary, the alkyl group contained in the alkoxy group may have the substituent as stated above.

An alkylthio group is the group corresponding to an alkoxy group. The alkyl group contained in the alkylthio group includes the alkyl group as stated above. For example, a lower alkylthio group includes a straight or branched lower alkylthio group, such as methylthio, ethylthio, n-propylthio, isopropylthio, n-butylthio, isobutylthio, sec-butylthio, tert-butyothio and pentylthio groups. Furthermore, if necessary, the alkyl group contained in the alkylthio group may have the substituent as stated above.

An amino group or a hydroxyl group may be protected by a protecting group. For example, the protecting group includes a (substituted) alkoxycarbonyl group such as t-butoxycarbonyl group (Boc) and 2,2,2-trichloroetoxycarbonyl groups; a (substituted) aralkyloxy-carbonyl group such as benzyloxycarbonyl, paramethoxybenzyloxycarbonyl, and paranitrobenzyloxycarbonyl groups; a (substituted) acyl group such as acethyl, methoxyacethyl, trifluoroacethyl, chloroacethyl, pivaloyl, formyl and benzoyl groups; a (substituted) alkyl or aralkyl group such as t-butyl, benzyl, paranitrobenzyl, paramethoxybenzyl and triphenylmethyl groups; a (substituted) ether group such as methoxymethyl, t-butoxymethyl, tetrahydropyranyl and 2,2,2-trichloroethoxymethyl groups; and an (alkyl and/or aralkyl) substituted silyl group such as trimethylsilyl, isopropyl dimethylsilyl, t-buryldimethylsilyl and tribenzylsilyl, t-buthyldiphenylsilyl groups. Herein, the term "(substituted)" means that something may have a substituent.

A protecting group of a carboxyl group (carboxyl protecting group) includes methyl, ethyl, n-propyl, isopropyl n-buthyl, isobutyl, sec-buthyl and tert-buthyl groups.

Especially, in Formula (I), $R_2$ is preferably a lower alkyl group such as a methyl or an ethyl group, or a halogen-substituted methyl or ethyl group thereof, a lower alkoxy group such as a methoxy or an ethoxy group, or a halogen-substituted methoxy group or ethoxy group thereof.

$R_3$ is also preferably a hydrogen atom, a halogen atom such as fluorine atom, or a lower alkoxy group such as a methoxy or an ethoxy group or a halogen-substituted methoxy or ethoxy group thereof.

Furthermore, $R_5$ is preferably a hydrogen atom, a lower alkyl group such as a methyl or an ethyl group or a halogen-substituted methyl or ethyl group thereof.

For example, a salt of the compound represented above by Formula (I) includes a salt of a mineral acid, e.g., hydrochloric, sulfuric and phosphoric acids, a salt of an organic carboxylic acid, e.g., tartaric, formic, acetic, citric, fumaric and lactic acids, a salt of a sulfonic acid, e.g., methansulfonic, benzensulfonic, p-toluensulfonic and mesithylensulfonic acids, a salt of an alkali metal, e.g., sodium and potassium, a salt of an alkaline earth metal, e.g., calcium and magnesium, and a salt of a nitrogen-containing organic base, e.g., ammonium salt.

The compound represented by Formula (I) or its salt includes also solvates, hydrates and various crystal forms.

Furthermore, the compound represented by Formula (I) includes the isomers. The isomers include optical isomers, steric isomers and geometric isomers.

Synthesis processes of the compound represented by Formula (I) (herein after referred to as the "present compound") will be explained below.

The present compound can be synthesized according to a known method. For example, the present compound can be synthesized according to Reaction Scheme 1 shown in FIG. 1.

For example, in Reaction Scheme 1, the compound of Formula (VI) can be synthesized from Compound (II) (2,3-dimethylpyridine) and Compound (V) (4-chloro-3-methoxy-2-methylpyridine) as starting materials which are commercially available.

Specifically, for example, Compound (III) can be obtained by dissolving Compound (II) in acetic acid solution and hydrogen peroxide being added thereto as an oxidizing agent, and then heating, for example, at 70 to 100° C. for 5 to 24 hours.

Compound (IV) can be obtained by nitrating Compound (III). The nitrating agent used herein includes a concentrated nitric acid, a mixed liquid of nitric acid and sulfuric acid, sulfuric acid and a nitrate such as potassium nitrate and sodium nitrate and anhydrous nitric acid.

Then, for example, when Compound (IV) is dissolved in concentrated nitric acid and heated, for example, at 120 to 160° C. for 5 to 12 hours in a closed tube, Compound (VI, $R_2$=a methyl group) can be obtained.

Then, moreover, Compound (VI, $R_2$=a methoxy group) can be obtained by dissolving Compound (V) in acetic acid and oxidized with hydrogen peroxide as stated above.

Compound (VI) wherein $R_2$ is difluoromethyl group, for example, is prepared from Compound (XVI) and via Compound (XVII) and Compound (XVIII) as stated in Reaction Scheme 1. Each of the reactions is known and it is thus easy to understand for those skilled in the art. Compound (XVI) can be easily produced by difloromethylating 2-methylpylidine-3-carbaldehyde which is commercially available with a fluorination agent such as diethylaminosulfur trifluoride by those skilled in the art (see Reference Examples 50 to 52). Compound (VI) wherein $R_2$ is difluoromethoxy group, for example, can also be produced by treating Compound (XIX) with 3-chloroperbenzoic acid as stated in Reaction Scheme 1 (see Reference Examples 30 to 37). This method is known to those skilled in the art. Compound (XIX) itself can be easily produced by, for example, difluoromethoxylating the 3-position hydroxyl group of maltol with chlorodifluoromethane, and then transforming it to the 4-oxopyridine skeleton by ammonia treatment and conducting chlorination using phosphoryl chloride by those skilled in the art.

Compound (VII) can be obtained by dissolving Compound (VI) in acetic anhydride, heating the resultant mixture, for example, at 70 to 110° C. for 0.5 to 5 hours, adding a base to the resulting residue and reacting it, for example, at 50 to 90° C. for 1 to 5 hours. The base used herein includes sodium hydroxide, potassium hydroxide and lithium hydroxide.

Compound (VIII) can be obtained by oxidizing Compound (VII). The oxidizing agent used herein includes dichromic acid-sulfuric acid, chromic oxide (VI)-pyridine complex, dimethylsulfoxide-oxalylchloride and dimethylsulfoxide-trifluoroacetic acid.

Then, Compound (IX) can be obtained by reacting Compound (VIII) with a Grignard reagent prepared from cyclopropyl bromide and magnesium. The reaction may be carried out, for example, at 0 to 50° C. for 1 to 15 hours.

Then, Compound (X) can be obtained by oxidizing Compound (IX) in the same manner as stated above.

Then, Compound (XI) can be obtained by reacting Compound (X) with a Wittig reagent which is prepared from (methoxymethyl)triphenylphosphonium chloride and a base. The base used herein includes phenyllithium, n-butyllithium and lithiumbis(trimethylsilyl)amide. The reaction may be carried out, for example, at 0 to 50° C. for 1 to 5 hours.

When Compound (XI) is hydrolyzed under the presence of an acid, Compound (XII) can be obtained. The acid used herein includes hydrochloric acid, hydrobromic acid, sulfuric acid and acetic acid. The reaction temperature may be, for example, at 40 to 80° C. and the reaction time may be, for example, for 2 to 5 hours.

Then, Knoevenagel condensation reaction of Compound (XII) with a diethyl malonate is carried out under the presence of an amine as a catalyst, an unsaturated carboxylic diester can be obtained as an intermediate product. The amine used herein includes piperidine, pyridine and diethylamine. The reaction temperature may be, for example, at 50 to 100° C. and the reaction time may be, for example, for 2 to 5 hours. When the intermediate product is dissolved in a high-boiling solvent such as diphenylether and Dowtherm A (a mixture of diphenylether and biphenyl) without purifying the intermediate product, and then heated, for example, at 200 to 250° C. for 0.5 to 2 hours, Compound (XIII) can be obtained (see Reference Examples 1 to 10).

The present compound (XIV) can be then obtained by reacting Compound (XIII) with Compound (3) in a solvent such as toluene under the presence of a catalyst such as bis(triphenylphosphine)palladium (II) chloride (see Example 1).

Then, the present compound (XV) can be obtained by hydrolyzing Compound (XIV) according to a conventional method (see Example 2).

The compound represented by Formula (II) used as a starting material can be synthesized by the method stated in J. Med. Chem., 38, 4906(1995), J. Pharm. Sci., 69, 1074 (1980), J. Org. Chem., 29, 776(1964) or by a similar method.

Figure 2:
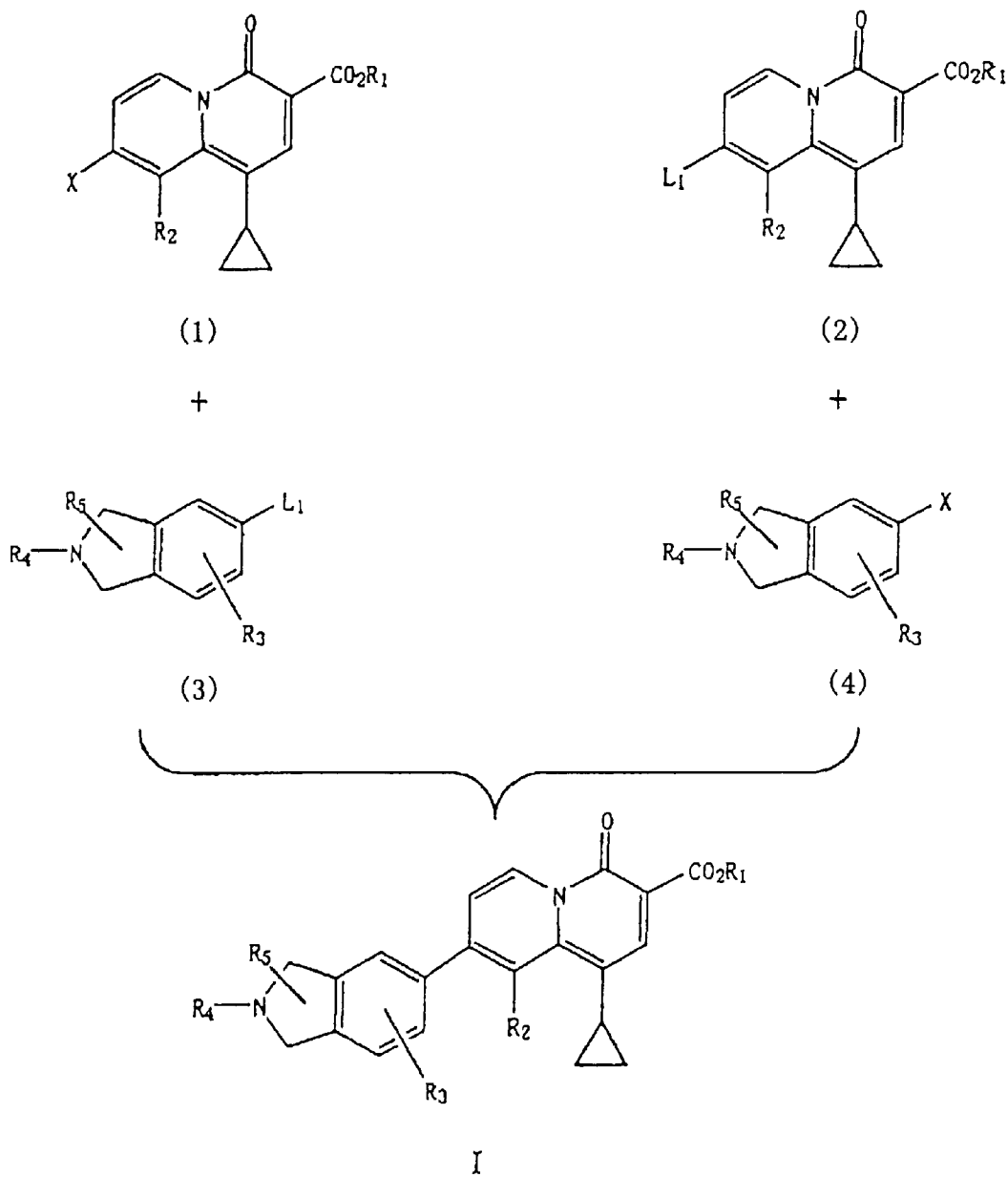
FIG. 2 shows Reaction Scheme 2.

The compound represented by Formula (I) can be also synthesized by the method according to Reaction Scheme 2 as shown in FIG. 2.

Herein, in Reaction Scheme 2, $R_1$ to $R_5$ are defined above, $L_1$ represents a tin(an alkyl group)$_3$ or a boron(a lower alkoxy group)$_2$ and X represents a halogen atom.

In Reaction Scheme 2, Compound (I) can be obtained by coupling Compound (1) with Organic tin compound (3) or coupling Organic tin compound (2) with Compound (4) under the presence of a palladium complex as a catalyst.

Any solvent can be used in the reaction, so long as the solvent does not affect the reaction. The solvents includes aromatic hydrocarbons such as benzene, toluene and xylene; ethers such as dioxane, tetrahydrofuran, anisole, diethyleneglycol diethylether and dimethylcellosolve; nitrites such as acetonitrile; amides such as N,N-dimethylformamide and N,N-dimethylacetoamide; and sulfoxides such as dimethylsulfoxide. The solvent may be used singly or as a mixture of two or more solvents.

The palladium complex catalyst used in the reaction includes $PdCl_2(PPh_3)_2$, $Pd(PPh_3)_4$, $PdCl_2(P(O\text{-toryl})_3)_2$, $PdCl_2+2P(OEt)_3$, and $PdCl_2(PhCN)_2$ wherein Ph represents a phenyl group and Et represents a ethyl group.

The amount of Organic tin compound (3) is the same molar or more as Compound (1), preferably 1.0 to 2.0 times molar to Compound (1).

The coupling reaction may usually be carried out, for example, at 50 to 170° C., for example, for 1 minute to 24 hours under an inert gas atmosphere such as argon or nitrogen.

Alternatively, Compound (I) can be obtained by coupling Compound (1) with Organic boron compound (3) by using the palladium complex catalyst in the same manner as stated above.

Any solvent can be used in the reaction, so long as it does not adversely effect the reaction, and includes water; alcohols such as methanol, ethanol and propanol; aromatic hydrocarbons such as benzene, toluene and xylene; hydrocarbon halogenides such as methylene chloride, chloroform and dichloroethane; ethers such as dioxane, tetrahydrofuran, anisole, diethyleneglycol diethylether and dimethylcellosolve; esters such as ethyl acetate and butyl acetate; ketones such as acetone and methylethylketone; nitrites such as acetonitrile; amides such as N,N-dimethylformamide and N,N-dimethylacetoamide; and sulfoxides such as dimethylsulfoxide. The solvent may be used singly or as a mixture of two or more solvents.

The base used in the reaction includes sodium hydrogencarbonate, sodium carbonate, potassium carbonate and triethylamine.

The amount of Organic boron compound (3) is the same molar or more as Compound (1), preferably 1.0 to 1.5 times molar to Compound (1).

The coupling reaction may usually be carried out at 50 to 170° C. for 1 minute to 24 hours under an inert gas atmosphere such as argon or nitrogen.

Moreover, the synthesis of Compounds (3) and (4) can be synthesized by the method shown in WO 9729102.

Figure 3:
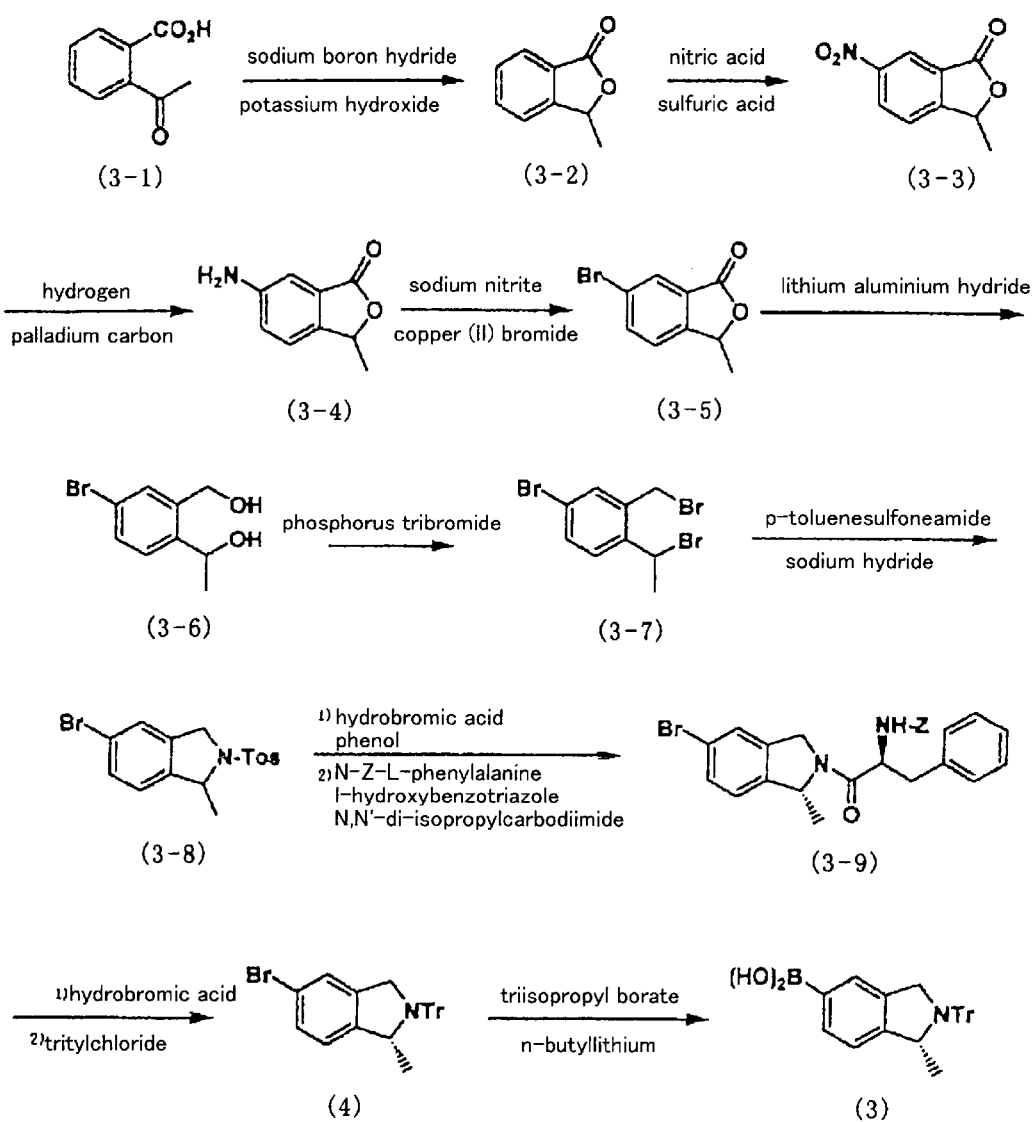
FIG. 3 shows Reaction Scheme 3.
Figure 4:
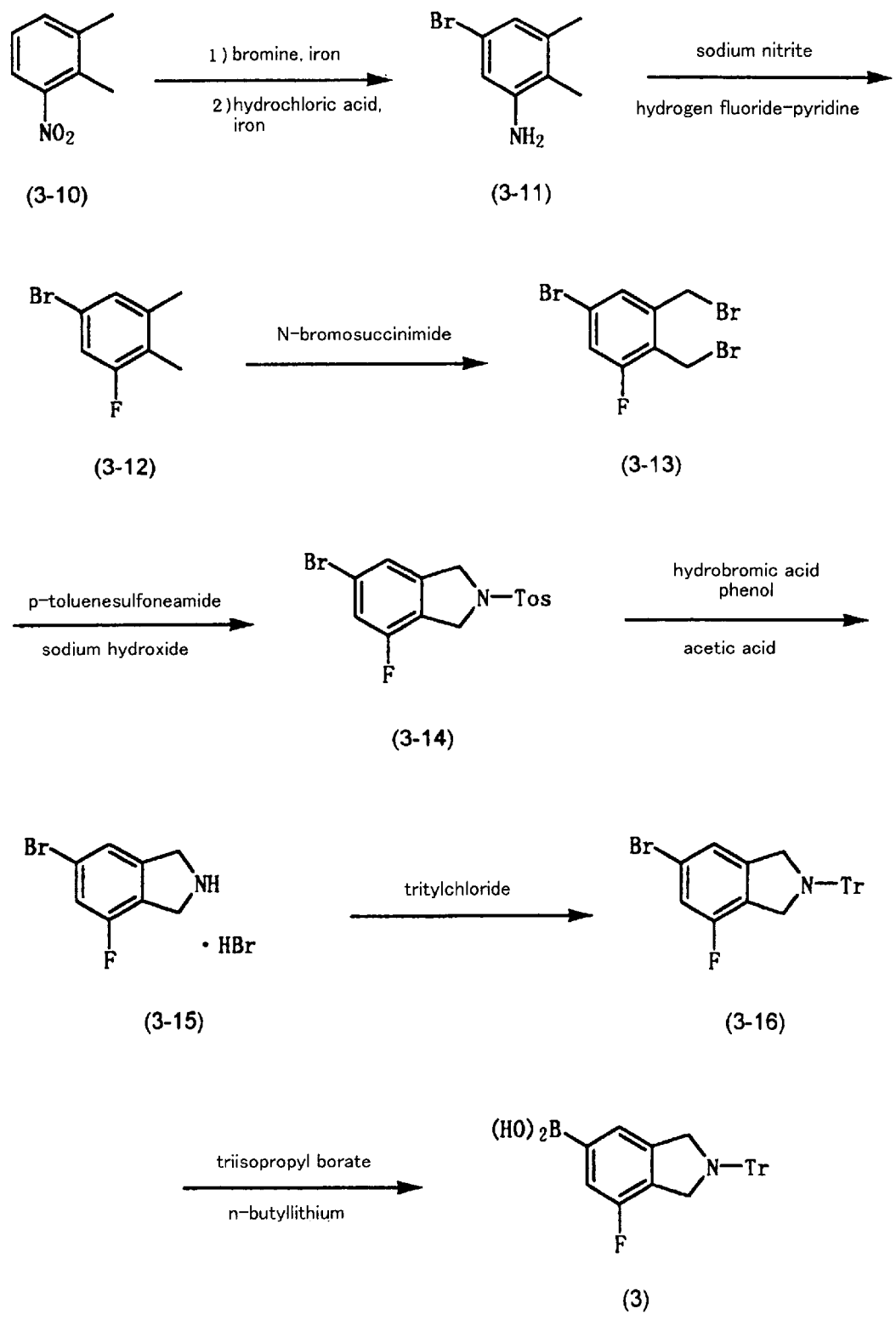
FIG. 4 shows Reaction Scheme 4.
Figure 5:
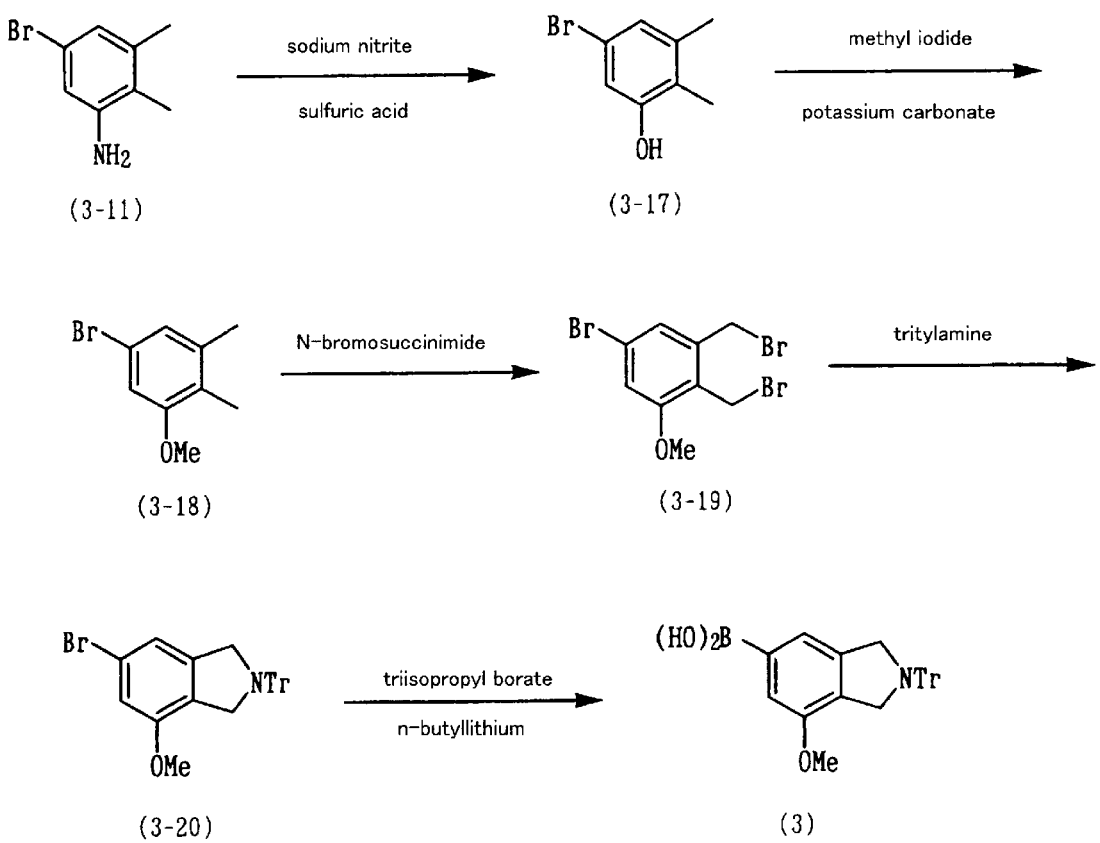
FIG. 5 shows Reaction Scheme 5.

Specifically, Compound (3) and (4) can be synthesized according to Reaction Scheme 3 shown in FIG. 3 (see Reference Examples 19 to 29).

For example, when Compound (3-1) is dissolved in a base and a reducing agent is added thereto, then stirred, for example, at 0 to 60° C. for 1 to 60 hours, and thereafter, the resultant mixture is oxidized with, for example, hydrochloric acid, to yield Compound (3-2). The base used herein includes sodium hydroxide, potassium hydroxide and lithium hydroxide. The reducing agent includes sodium boron hydride and potassium boron hydride.

Then, Compound (3-3) can be obtained by nitrifying Compound (3-2). The nitrating agent includes a concentrated nitric acid, a mixture of nitric acid and sulfuric acid, sulfuric acid and nitrate such as potassium nitrate and sodium nitrate, and anhydrous nitric acid.

Then, Compound (3-4) can be obtained by dissolving Compound (3-3), for example, in ethanol and adding a catalyst thereto and reducing the resultant mixture under a hydrogen atmosphere. The catalyst used herein includes palladium carbon and Raney nickel. The hydrogen pressure may be usual pressure or pressurized. The reaction temperature may be, for example, at −5 to 50° C. and the reaction time may be, for example, for 1 to 30 hours. The reaction may be carried out by reducing with a metal such as tin and iron under the presence of a hydrochloric acid.

Then, Compound (3-5) can be obtained by halogenating Compound (3-4). The method of the halogenation may be carried out by Sandmeyer reaction by which the corresponding diazonium salt to Compound (3-4) is brominated by copper bromide.

Then, Compound (3-6) can be obtained by adding a reducing agent to Compound (3-5) in anhydrous THF and reducing the resultant mixture, for example, at −78 to 0° C. for 1 to 12 hours. The reducing agent used herein includes lithium aluminum hydride, diisobuthylalminium hydride and borane.

Then, Compound (3-7) can be obtained by halogenating Compound (3-6). The halogenating agent used herein includes phosphorous tribromide, hydrobromic acid, phosphorus oxychloride, and thionyl chloride. The reaction temperature is, for example, at −5 to 50° C. and the reaction time is, for example, for 1 to 30 hours.

Then, Compound (3-8) can be obtained by dissolving Compound (3-7) in, for example, anhydrous DMF and reacting the resultant mixture, for example, with p-toluensulfonamide under the presence of a base. The base used herein includes sodium hydride, sodium ethoxide and n-buthyl lithium. The reaction temperature is, for example, at 30 to 180° C. and the reaction time is, for example, for 0.5 to 12 hours.

Then, Compound (3-9) can be obtained by heating Compound (3-8), for example, at 30 to 180° C., for example, for 1 to 12 hours under the presence of a mineral acid and an organic acid and then reacting it with a N-Z-L-phenylalanine, for example, at 0 to 80° C. for 1 to 30 hours. The mineral acid used herein includes a hydrochloric acid, a hydrobromic acid and a sulfuric acid. The organic acid includes acetic acid, propionic acid, p-toluensulfonic acid and phenol. In the condensation of Compound (3-8) with a N-Z-L-phenylalanine wherein Z is a benzyloxycarbonyl group, the appropriate active esterification agent and condensation agent can be used. The active esterification agent includes N-hydroxysuccinimide and 1-hydroxybenzotriazol. The condensation agent includes N,N'-dicyclohexylcarbodiimide and N,N'-diisopropylcarbodiimide.

Compound (4) can be obtained by heating Compound (3-9), for example, at 50 to 180° C., for example, for 1 to 80 hours under the presence of an inorganic acid or an organic acid and reacting it with tritylchloride, for example, at 0 to 50° C., for example, for 1 to 30 hours under the presence of a base. The inorganic acid used herein includes hydrochloric acid, hydrobromic acid and sulfuric acid. The organic acid includes acetic acid and phenol. The base includes potassium carbonate, sodium hydroxide, ammonia and triethylamine.

Then, Compound (3) can be obtained by dissolving Compound (4), for example, in anhydrous THF, and reacting the resultant mixture, for example, with a trialkyl borate under inactive atomsphere such as argone and the presence of a base. The base used herein includes n-butyl lithium, phenyl lithium, lithium diisopropylamide and lithium bis (trimethylsilyl)amide. The trialkyl borate includes trimethyl borate, triethyl borate and triisopropyl borate. The reaction temperature is, for example, at −100 to −15° C. and the reaction time is, for example, for 2 to 30 hours.

Compound (3) wherein $R_3$ is fluorine atom may be synthesized by the method as stated in Reaction Scheme 4. For the specific synthetic route, see Reference Examples 38 to 44.

Compound (3) wherein $R_3$ is a methoxy group may be synthesized by the method as stated in Reaction Scheme 5. For the specific synthetic route, see Reference examples 45 to 49.

As stated above, each kind of substitutent may be introduced into the present compound as $R_2$ of Compound (1) or (2), or as $R_3$ of Compound (3) or (4) in Reaction Scheme 2. It is also possible for those skilled in the art to think of various modifications of the present embodiment based on the disclosure of the present invention.

The present compound is a useful antimicrobial agent for curing local infections or general infections of a human and an animal caused by, e.g., Gram-positive, Gram-negative bacteria and anaerobic bacteria.

The present compound can be used singly or with an adjuvant, a diluent, a binder and the like which is pharmaceutically acceptable, in a form of a general pharmaceutical composition such as a tablet, frosted tablet, capsule, injection, cream, ointment, liquid and powder. The present compound can be used singly or as a mixture of multiple different compounds.

In an oral reagent and a suppository, a pharmaceutical component, for example, an excipient such as lactose, D-mannitol, cornstarch and crystal cellulose, a disintegrator such as carboxymethylcellulose and carboxymethylcellulose calcium, a binder such as hydroxypropylcellulose, hydroxypropylmethylcellulose and polyvinylpyrrolidone, a lubricant such as magnesium stearate and talc, a coating agent such as hydroxypropylmethylcellulose, white sugar and titanium oxide, a plasticizer such as polyethylene glycol, a base such as polyethylene glycol and hard fat may be used. In an injection, an eye drop and an ear drop, a pharmaceutical component including, for example, a solubilizer or a solubilizer adjuvant which can be constituted in an aqueous or necessary dissolution formulation such as distilled water for injection, saline and propylene glycol, a pH adjuster such as inorganic acid, organic acid or base, an isotonic agent such as saline, glucose and glycerin, and a stabilizer may be used. In an eye ointment and a dermatologic medicine, an appropriate pharmaceutical component as an ointment, a cream and a patch, for example, white vaseline, macrogol, glycerin, liquid paraffin and cotton cloth may be used.

A dosage of the present compound is varied depending on the symptoms, age and weight of a patient and the like. Usually, in the case of a general administration, it is possible to administer the compound to an adult in a proportion of 0.05 to 100 mg/kg/day, preferably 0.1 to 50 mg/kg/day. For example, a concentration of the effective component in a local cure is 0.01 to 5%, preferably 0.1 to 3%.

EXAMPLE

The present invention will be explained in more detail below referring to Examples and Reference Examples, however, the present invention should not be construed to be limited thereto.

Reference Example 1
(See Reaction Scheme 1)

71.79 g of 2,3-dimethylpyridine (II) was dissolved in 240 ml of acetic acid, to which 40 ml of 30% hydrogen peroxide solution was added and the resulting mixture was heated at 95° C. for 3 hours. Furthermore, 18 ml of a 30% hydrogen peroxide solution was added to the mixture and heated at 95° C. for 13 hours, and thereafter, 700 ml of water was added thereto and the resulting mixture was neutralized with sodium carbonate and extracted with chloroform. The resulting organic layer was dried over anhydrous sodium sulfate and the solvent was distilled off under reduced pressure. The resulting precipitation was recrystallized from diisopropylether to obtain 71.34 g of 2,3-dimethylpyridine N-oxide (III).

$^1$H-NMR(CDCl$_3$) δ: 2.35(3H, s), 2.51(3H, s), 6.95–7.10 (2H, m), 8.10–8.17(1H, m)

Reference Example 2

4.40 g of 2,3-dimethylpyridine N-oxide (III) was dissolved in 9 ml of concentrated sulfuric acid and the mixture of 13 ml of concentrated sulfuric acid and 15 ml of 65% nitric acid was added thereto and the resulting mixture was heated at 95° C. for 11 hours. The reaction solution was poured into ice water, and neutralized with 8N sodium hydroxide, and thereafter, extracted with chloroform. The resulting organic layer was dried over anhydrous sodium sulfate and the solvent was distilled off under reduced pressure. The resulting residue was purified by silica gel column chromatography (eluent; chloroform:methanol= 20:1) to obtain 3.71 g of 2,3-dimethylpyridine-4-nitro-N-oxide (IV).

$^1$H-NMR(CDCl$_3$) δ:2.57(3H, s), 2.59(3H, s), 7.72(1H, d, J=7.1 Hz), 8.21(1H, d, J=7.1 Hz)

Reference Example 3

5.19 g of 2,3-dimethylpyridine-4-nitro-N-oxide (IV) was dissolved in 50 ml of concentrated hydrochloric acid, and in a closed tube, the resulting mixture was heated at 160° C. for 9 hours. The solvent was distilled off under reduced pressure, and thereafter, the resulting residue was purified by silica gel column chromatography (eluent; chloroform:methanol=20:1) to obtain 4.40 g of 4-chloro-2, 3-dimethylpyridine-N-oxide (VI).

$^1$H-NMR(CDCl$_3$) δ:2.40(3H, s), 2.57(3H, s), 7.14(1H, d, J=6.8 Hz), 8.09(1H, d, J=6.8 Hz)

EI-MS m/z: 157(M$^+$)

Reference Example 4

50 ml of acetic anhydride was added to 5.63 g of 4-chloro-2,3-dimethylpyridine-N-oxide (VI) and the resulting mixture was heated at 110° C. for 1 hour. The solvent was distilled off under reduced pressure and water was added thereto and the resulting mixture was extracted with ether. The resulting organic layer was washed with water and dried over anhydrous sodium sulfate and the solvent was distilled off under reduced pressure. The resulting residue was dissolved in 90% ethanol, and 2.10 g of sodium hydroxide was added thereto, and the resulting mixture was heated at 80° C. for 3 hours. The solvent was distilled off under reduced pressure, and thereafter, water was added thereto and the resulting mixture was extracted with chloroform. The resulting organic layer was washed with saturated salt water, and then dried over anhydrous sodium sulfate and the solvent was distilled off under reduced pressure. The resulting residue was purified by silica gel column chromatography (eluent; chloroform) to obtain 1.69 g of 4-chloro-2-hydroxymethyl-3-methylpyridine (VII).

$^1$H-NMR(DMSO-d$_6$) δ: 2.36(3H, s), 4.62(2H, d, J=5.6Hz), 5.20(1H, t, J=5.6 Hz), 7.44(1H, d, J=5.1 Hz), 8.30(1H, d, J=5.1 Hz)

EI-MS m/z: 157(M$^+$)

Reference Example 5

17.2 ml of oxalyl chloride solution was dissolved in 350 ml of anhydrous dichloromethane, and under cooling at −78° C., 150 ml of anhydrous dichloromethane solution of 15.1 ml of anhydrous dimethylsulfoxide was dropped thereto. The resulting mixture was stirred at −78° C. for 40 minutes, and thereafter, 300 ml of anhydrous dichloromethane solution of 23.92 g of 4-chloro-2-hyrdoxymethyl-3-methylpyridine (VII) was dropped thereto. The resulting mixture was stirred at −78° C. for 30 minutes, and thereafter, the reaction temperature was elevated to −45° C., and was stirred at the same temperature for 1 hour, and thereafter, 105.8 ml of triethylamine was dropped thereto and the temperature of the resulting mixture was elevated to a room temperature. Water was added to the resulting mixture, and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; chloroform) to obtain 19.31 g (4-chloro-3-methylpyridine)-2-carbardehyde (VIII).

$^1$H-NMR(CDCl$_3$) δ:2.73(3H, s), 7.50(1H, d, J=5.1 Hz), 8.55(1H, d, J=5.1 Hz), 10.17(1H, s)

Reference Example 6

150 ml of a THF solution of 19.30 g of (4-chloro-3-methylpyridine)-2-carbardehyde (VIII) was dropped to 180 ml of THF solution of magnesium cyclopropyl bromide which was prepared from 14.9 ml of cyclopropyl bromide and 4.53 g of magnesium. The resulting mixture was stirred at a room temperature for 12 hours, and poured into saturated ammonium chloride solution and extracted with chloroform. The resulting organic layer was washed with saturated salt water and dried over anhydrous sodium sulfate and the solvent was distilled off under reduced pressure. The resulting residue was purified by silica gel column chromatography (eluent; hexane:ethyl acetate=3:1) to obtain 19.58 g of (4-chloro-3-methyl-2-pyridyl)cyclopropylmethane-1-ol (IX).

$^1$H-NMR(CDCl$_3$) δ: 0.30–0.61(4H, m), 1.10–1.20(1H, m), 2.40(3H, s), 4.50(1H, d, J=7.8 Hz), 4.78–4.80(1H, m), 7.25(1H, d, J=5.4 Hz), 8.27(1H, d, J=5.4 Hz)

Reference Example 7

11.22 ml of oxalyl chloride was dissolved in 300 ml of anhydrous dichloromethane, and under cooling at −78° C., 100 ml of anhydrous dichloromethane solution of 9.83 ml of anhydrous dimethylsulfoxide was dropped thereto. The resulting mixture was stirred at −78° C. for 40 minutes, and thereafter, 200 ml of anhydrous dichloromethane solution of 19.55 g of (4-chloro-3-methyl-2-pyridyl) cyclopropylmethane-1-ol (IX) was dropped thereto. The resulting mixture was stirred at −78° C. for 30 minutes, and thereafter, the reaction temperature was elevated to −45° C. and the resulting mixture was stirred at the same temperature for 1 hour, and thereafter, 68.93 ml of triethylamine was dropped thereto and the temperature of the resulting mixture was elevated to a room temperature. Water was added thereto and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; hexane: ethyl acetate=19:1) to obtain 17.89 g of (4-chloro-3-methyl-2-pyridyl)cyclopropylketone (X).

$^1$H-NMR(CDCl$_3$) δ: 1.10–1.20(2H, m), 1.25–1.30(2H, m), 2.53(3H, s), 2.95–3.10(1H, m), 7.43(1H, d, J=5.1 Hz), 8.41(1H, d, J=5.1 Hz)

Reference Example 8

5.54 g of (methoxymethyl) triphenyl phosphonium chloride is suspended in 53 ml of anhydrous ether and 18.4 ml of phenyllithium (0.88 M) was dropped thereto and the resulting mixture was stirred at a room temperature for 15 minutes. 35 ml of ether solution of 3.01 g of (4-chloro-3-methyl-2-pyridyl)cyclopropylketone (X) was dropped thereto and the resulting mixture was stirred at a room temperature for 2 hours. The resulting residue was separated by filtering and washed with ether, and thereafter, the ether filtrate and ether used for washing were collected together and the collected solution was washed with water, and thereafter, dried over anhydrous sodium sulfate and the solvent was distilled off under reduced pressure. The resulting residue was purified by silica gel column chromatography (eluent; hexane:ethyl acetate=4:1) to obtain 1.66 g of 2-(4-chloro-3-methyl-2-pyridyl)-2-cyclopropyl-1-methoxyethene.

$^1$H-NMR(CDCl$_3$)

δ$_1$: 0.25–0.30(2H, m), 0.70–0.74(2H, m), 1.90–2.00(1H, m), 2.39(3H, s), 3.71(3H, s), 6.15(1H, d, J=1.0 Hz), 7.16 (1H, d, J=5.6 Hz), 8.24(1H, d, J=5.6 Hz)

δ$_2$: 0.30–0.40(2H, m), 0.60–0.65(2H, m), 1.60–1.70(1H, m), 2.29(3H, s), 3.56(3H, s), 6.11(1H, d, J=1.2 Hz), 7.16(1H, d, J=5.6 Hz), 8.33(1H, d, J=5.6 Hz)

Reference Example 9

1.66 g of 2-(4-chloro-3-methyl-2-pyridyl)-2-cyclopropyl-1-methoxyethene (XI) was dissolved in 16 ml of THF and 16 ml of dilute sulfuric acid was added to the resulting mixture, which was concentrated at 50° C. under reduced pressure. The resulting mixture was poured into water and neutralized with saturated sodium bicarbonate solution, and thereafter, extracted with chloroform. The resulting organic layer was washed with saturated salt water, and thereafter, dried over anhydrous sodium sulfate and the solvent was distilled off under reduced pressure. The resulting residue was purified by silica gel column chromatography (eluent; hexane:ethyl acetate=4:1) to obtain 1.31 g of 2-(4-chloro-3-methyl-2-pyridyl)-2-cyclopropylethanal (XII).

$^1$H-NMR(CDCl$_3$) δ: 0.23–0.78(4H, m), 1.50–1.60(1H, m), 2.36(3H, s), 3.20–3.30(1H, m), 7.24(1H, d, J=5.1 Hz), 8.35(1H, d, J=5.1 Hz), 9.87(1H, d, J=2.7 Hz)

Reference Example 10

1.31 g of 2-(4-chloro-3-methyl-2-pyridyl)-2-cyclopropylethanal (XII) was dissolved in 45 ml of anhydrous ethanol, and 1.48 ml of piperidine, 1.48 ml of acetic acid and 4.75 ml of diethylmalonate were added thereto and the resulting mixture was heated at 100° C. for 5 hours. The solvent was distilled off under reduced pressure, and thereafter, the resulting mixture was diluted with ether and the resulting organic layer was washed with water and saturated salt water, and thereafter, dried over anhydrous sodium sulfate and the solvent was distilled off under reduced pressure. 30 ml of Dowtherm A was added to the resulting residue, which was heated at 240° C. for 30 minutes. The reaction solution was purified directly by silica gel column chromatography (eluent; hexane hexane:ethyl acetate=1:1) to obtain 1.45 g of ethyl 8-chloro-1-cyclopropyl-9-methyl-4-oxo-4H-quinolizine-3-carboxylate (XIII).

$^1$H-NMR(CDCl$_3$) δ: 0.70–0.75(2H, m), 1.00–1.10(2H, m), 1.42(3H, t, J=7.1 Hz), 2.25–2.30 (1H, m), 3.00(3H, s), 4.42(2H, q, J=7.1 Hz), 7.11(1H, d, J=7.8 Hz), 8.39(1H, s), 9.31(1H, d, J=7.8 Hz)

Example 1
(See Reaction Scheme 1)

226.8 mg of ethyl 8-chloro-1-cyclopropyl-9-methyl-4-oxo-4H-quinolizine-3-carboxylate (XIII) was suspended in 3 ml of toluene, and 1.6 ml of ethanol, 0.82 ml of a 2M sodium carbonate solution, 311.1 mg of (+)-1-methyl-2-tritylisoindoline-5-boric acid (3) and 23.2 mg of bis(triphenylphosphin)paradium (II) chloride were added thereto, and thereafter, under an argon atmosphere, the resulting mixture was heated under reflux for 4 hours. Ethyl acetate was added to the reaction solution and the organic layer was separated and rinsed with water, and thereafter, dried over anhydrous sodium sulfate and the solvent was distilled off under reduced pressure. The resulting residue was purified by silica gel column chromatography (eluent; hexane:ethyl acetate=1:1) to obtain 335.9 mg of ethyl 1-cyclopropyl-9-methyl-8-(1-methylisoindoline-5-yl)-4-oxo-4H-quinolizine-3-carboxylate (XIV).

$^1$H-NMR(CDCl$_3$) δ: 0.70–0.76(2H, m), 0.95–1.05(2H, m), 1.43(3H, t, J=7.1 Hz), 1.49(3H, d, J=6.6 Hz), 2.30–2.40 (1H, m), 2.62(3H, s), 4.10–4.61(5H, m), 6.60–7.58 (19H, m), 8.31(1H, s), 9.39(1H, d, J=7.6Hz)

Example 2
(See Reaction Scheme 1)

7.6 ml ethanol, 2.5 ml of THF and 1.3 ml of 1N hydrochloric acid were added to 312.5 mg of ethyl 1-cyclopropyl-9-methyl-8-(1-methylisoindoline-5-yl)-4-oxo-4H-quinolizine-3-carboxylate (XIV) and the resulting mixture was stirred at room temperature for 30 minutes. The solvent was distilled off under reduced pressure and water was added to the resulting residue and the resulting residue was washed with ethyl acetate, and thereafter, the resulting water layer was concentrated under reduced pressure. 10 ml of water, 5 ml of ethanol and 3 ml of 1N sodium hydroxide were added to the residue, which was stirred at 50° C. for 3 hours. The reaction solution was concentrated under reduced pressure, and thereafter, dissolved in 4 ml of water and neutralized with 1N hydrochloric acid. The precipitated crystal was separated by filtering to obtain 139.1 mg of 1-cyclopropyl-9-methyl-8-(1-methylisoindoline-5-yl)-4-oxo-4H-quinolizine-3-carboxylic acid.

$^1$H-NMR(DMSO-d$_6$) δ: 0.75–0.80(2H, m), 1.00–1.10 (2H, m), 1.38(3H, d, J=6.4 Hz), 2.40–2.55(1H, m), 2.86(3H, s), 4.09–4.44(3H, m), 7.30–7.50(3H, m), 7.54(1H, d, J=7.6 Hz), 8.26 (1H, s), 9.31(1H, d, J=7.6 Hz)

FAB–MS m/z: 375(M+H)$^+$

Reference Example 11
(See Reaction Scheme 1)

36.98 g of 4-chloro-3-methoxy-2-methylpyridine (V) was dissolved in 685 ml of acetic acid and 92 ml of hydrogen peroxide water was added thereto and the resulting mixture was heated at 90° C. for 24 hours, and thereafter, the reaction solution was distilled off under reduced pressure. The resulting residue was dissolved in chloroform and washed with saturated sodium bicarbonate solution, and saturated salt water, and thereafter, dried over anhydrous sodium sulfate. The solvent was distilled off under reduced pressure to obtain 37.64 g of 4-chloro-3-methoxy-2-methylpyridine N-oxide (VI).

$^1$H-NMR(CDCl$_3$) δ:2.52(3H, s), 3.88(3H, s), 7.13(1H, d, J=7.1 Hz), 8.05(1H, d, J=7.1 Hz)

Reference Example 12

175 ml of acetic anhydride was added to 37.64 g of 4-chloro-3-methoxy-2-methylpyridine-N-oxide (VI) and the resulting mixture was heated at 110° C. for 1 hour. The solvent was distilled off under reduced pressure, and thereafter, 3N sodium hydroxide solution was added thereto and the resulting mixture was adjusted to pH 11 and heated at 80° C. for 4 hours. The resulting mixture was extracted with chloroform and the resulting organic layer was washed with saturated salt water, and thereafter, dried over anhydrous sodium sulfate, and the solvent was distilled off under reduced pressure. The resulting residue was purified by silica gel column chromatography (eluent; chloroform:ethyl acetate=5:1) to obtain 24.10 g of 4-chloro-2-hydroxymethyl-3-methoxypyridine(VIII).

$^1$H-NMR(CDCl$_3$) δ: 3.91(3H, s), 4.18(1H, brs), 4.81(2H, s), 7.28(1H, d, J=5.1 Hz), 8.22(1H, d, J=5.1 Hz)

Reference Example 13

15.5 ml of oxalyl chloride was dissolved in 300 ml of anhydrous dichloromethane, and under cooling at −78° C., 150 ml of anhydrous dichloromethane solution of 13.5 ml of anhydrous dimethylsulfoxide was dropped thereto. The resulting mixture was stirred at −78° C. for 40 minutes, and thereafter, 300 ml of anhydrous dichloromethane solution of 23.66 g of 4-chloro-2-hyrdoxymethyl-3-methoxypyridine (VII) was dropped thereto. The resulting mixture was stirred at −78° C. for 30 minutes, and thereafter, the reaction temperature was elevated to −45° C., and the resulting mixture was stirred at the same temperature for 1 hour, and thereafter, 95.0 ml of triethylamine was dropped thereto and the temperature of the resulting mixture was elevated to a room temperature. Water was added to the resulting mixture, and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; chloroform:ethyl acetate=5:1) to obtain 20.60 g (4-chloro-3-methoxypyridine)-2-carbardehyde (VIII).

$^1$H-NMR(CDCl$_3$) δ:4.03(3H, s), 7.57(1H, d, J=4.9 Hz), 8.47(1H, d, J=4.9 Hz), 10.24(1H, s)

Reference Example 14

25 ml of THF solution of 3.45 g of (4-chloro-3-methoxypyridine)-2-carbardehyde (VIII) was dropped to 35 ml of THF solution of magnesium cyclopropyl bromide which was prepared from 2.42 ml of cyclopropyl bromide and 0.73 g of magnesium. The resulting mixture was stirred at a room temperature for 12 hours, and poured into saturated ammonium chloride and extracted with chloroform. The resulting organic layer was washed with saturated salt water and dried over anhydrous sodium sulfate and the solvent was distilled off under reduced pressure. The resulting residue was purified by silica gel column chromatography (eluent; chloroform) to obtain 3.26 g of (4-chloro-3-methoxy-2-pyridyl)cyclopropylmethane-1-ol (IX).

$^1$H-NMR(CDCl$_3$) δ: 0.40–0.61(4H, m), 1.10–1.27(1H, m), 3.93(3H, s), 4.20(1H, brs), 4.62 (1H, brs), 7.28(1H, d, J=5.1 Hz), 8.23(1H, d, J=5.1 Hz)

Reference Example 15

10.22 ml of oxalyl chloride was dissolved in 300 ml of anhydrous dichloromethane, and under cooling at −78° C., 100 ml of anhydrous dichloromethane solution of 8.95 ml of anhydrous dimethylsulfoxide was dropped thereto. The resulting mixture was stirred at −78° C. for 40 minutes, and thereafter, 200 ml of anhydrous dichloromethane solution of 19.25 g of (4-chloro-3-methoxy-2-pyridyl) cyclopropylmethane-1-ol (IX) was dropped thereto. The resulting mixture was stirred at −78° C. for 30 minutes, and thereafter, the reaction temperature was elevated to −45° C. and the resulting mixture was stirred at the same temperature for 1 hour, and thereafter, 62.79 ml of triethylamine was dropped and the temperature of the resulting mixture was elevated to a room temperature. Water was added thereto and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; chloroform:ethyl acetate= 20:1) to obtain 17.27 g of (4-chloro-3-methoxy-2-pyridyl) cyclopropylketone (X).

$^1$H-NMR(CDCl$_3$) δ: 1.09–1.30(4H,m), 2.90–2.97(1H, m), 3.95(3H, s), 7.48(1H, d, J=5.1 Hz), 8.33(1H, d, J=5.1 Hz)

Reference Example 16

30.78 g of (methoxymethyl) triphenyl phosphonium chloride is suspended in 300 ml of anhydrous ether and 102 ml of phenyllithium (0.88 M) was dropped thereto and the resulting mixture was stirred at a room temperature for 15 minutes. 210 ml of ether solution of 18.10 g of (4-chloro-3-methoxy-2-pyridyl)cyclopropylketone (X) was dropped thereto and was stirred at a room temperature for 12 hours. The resulting residue was separated by filtering and washed with ether, and thereafter, the ether filtrate and ether used for washing were collected together and the collected solution was washed with water, and thereafter, dried over anhydrous sodium sulfate and the solvent was distilled off under reduced pressure. The resulting residue was purified by silica gel column chromatography (eluent; hexane:ethyl acetate=4:1) to obtain 8.94 g of 2-(4-chloro-3-methoxy-2-pyridyl)-2-cyclopropyl-1-methoxyethene (XI).

$^1$H-NMR(CDCl$_3$)

δ$_1$: 0.47–0.51(2H, m), 0.71–0.75(2H, m), 1.83–1.91(1H, m), 3.76(3H, s), 3.82(3H, s), 6.57(1H, d, J=1.2 Hz), 7.16 (1H, d, J=5.1 Hz), 8.15(1H, d, J=5.1 Hz)

δ$_2$: 0.41–0.45(2H, m), 0.57–0.62(2H, m), 1.63–1.70(1H, m), 3.58(3H, s), 3.85(3H, s), 6.20(1H, d, J=1.2 Hz), 7.22 (1H, d, J=5.1 Hz), 8.26(1H, d, J=5.1 Hz)

Reference Example 17

1.02 g of 2-(4-chloro-3-methoxy-2-pyridyl)-2-cyclopropyl-1-methoxyethene (XI) was dissolved in 10 ml of THF and 10 ml of dilute sulfuric acid was added to the resulting mixture and the resulting mixture was concentrated at 50° C. under reduced pressure. The resulting mixture was poured into water and neutralized with saturated sodium bicarbonate solution, and thereafter, extracted with chloroform. The resulting organic layer was washed with saturated salt water, and thereafter, dried over anhydrous sodium sulfate and the solvent was distilled off under reduced pressure. The resulting residue was purified by silica gel column chromatography (eluent; hexane:ethyl acetate=4:1) to obtain 0.81 g of 2-(4-chloro-3-methyl-2-pyridyl)-2-cyclopropylethanal (XII).

$^1$H-NMR(CDCl$_3$) δ: 0.23–0.82(4H, m), 1.50–1.59(1H, m), 3.23–3.26(1H, m), 3.86(3H, s), 7.27(1H, d, J=5.1 Hz), 8.27(1H, d, J=5.1 Hz), 9.92(1H, d, J=2.7 Hz)

Reference Example 18

0.85 g of 2-(4-chloro-3-methoxy-2-pyridyl)-2-cyclopropylethanal (XII) was dissolved in 27 ml of anhydrous ethanol, and 0.89 ml of piperidine, 0.89 ml of acetic acid and 2.85 ml of diethylmalonate were added thereto and the resulting mixture was heated at 100° C. for 5.5 hours. The solvent was distilled off under reduced pressure, and thereafter, the resulting mixture was diluted with ether and the resulting organic layer was washed with water and saturated salt water, and thereafter, dried over anhydrous sodium sulfate and the solvent was distilled off under reduced pressure. 20 ml of Dowtherm A was added to the resulting residue and the resulting mixture was heated at 240° C. for 30 minutes. The reaction solution was purified directly by silica gel column chromatography (eluent; hexane→hexane:ethyl acetate=1:1) to obtain 0.67 g of ethyl 8-chloro-1-cyclopropyl-9-methoxy-4-oxo-4H-quinolizine-3-carboxylate (XIII).

$^1$H-NMR(CDCl$_3$) δ: 0.74–0.75(2H, m), 0.95–1.02(2H, m), 1.42(3H, t, J=7.3 Hz), 2.45–2.55 (1H, m), 3.97(3H, s), 4.42(2H, q, J=7.3 Hz), 7.10(1H, d, J=7.8 Hz), 8.26(1H, s), 9.26(1H, d, J=7.8 Hz)

Example 3
(See Reaction Scheme 1)

153.5 mg of ethyl 8-chloro-1-cyclopropyl-9-methoxy-4-oxo-4H-quinolizine-3-carboxylate (XIII) was suspended in 2.0 ml of toluene, and 1.0 ml of ethanol, 0.5 ml of 2M sodium carbonate solution, 200.0 mg of (+)-1-methyl-2-tritylisoindoline-5-boric acid (3) and 15.0 mg of bis (triphenylphosphin)paradium (II) chloride were added thereto, and thereafter, under an argon atmosphere, the resulting mixture was heated under reflux for 4 hours. Ethyl acetate was added to the reaction solution and the organic layer was separated and rinsed with water, and thereafter, dried over anhydrous sodium sulfate and the solvent was distilled off under reduced pressure. The resulting residue was purified directly by silica gel column chromatography (eluent; chloroform:ethyl acetate=5:1) to obtain 248.2 mg of ethyl 1-cyclopropyl-9-methoxy-8-(1-methyl-2-tritylisoindoline-5-yl)-4-oxo-4H-quinolizine-3-carboxylate (XIV).

$^1$H-NMR(CDCl$_3$) δ: 0.73–0.78(2H, m), 0.90–0.98(2H, m), 1.42(3H, t, J=7.1 Hz), 1.48(3H, d, J=6.6 Hz), 2.49–2.58 (1H, m), 3.28(3H, s), 4.15–4.63(5H, m), 6.88–7.59(19H, m), 8.23(1H, s), 9.31(1H, d, J=7.6 Hz)

Example 4

6.0 ml ethanol, 2.0 ml of THF and 1.0 ml of 1N hydrochloric acid were added to 248.0 mg of ethyl 1-cyclopropyl-9-methoxy-8-(1-methyl-2-tritylisoindoline-5-yl)-4-oxo-4H-quinolizine-3-carboxylate (XIV) and the resulting mixture was stirred at a room temperature for 30 minutes. The solvent was distilled off under reduced pressure and water was added to the resulting residue, which was washed with ethyl acetate, and thereafter, the resulting water layer was concentrated under reduced pressure. 10 ml of water, 5 ml of ethanol and 3 ml of 1N sodium hydroxide were added to the residue and the resulting mixture was stirred at 50° C. for 3 hours. The reaction solution was concentrated under reduced pressure, and thereafter, dissolved in 4 ml of water and neutralized with 1N hydrochloric acid. The precipitated crystal was separated by filtering to obtain 99.1 mg of 1-cyclopropyl-9-methoxy-8-(1-methylisoindoline-5-yl)-4-oxo-4H-quinolizine-3-carboxylic acid.

$^1$H-NMR(DMSO-d$_6$) δ: 0.75–0.76(2H, m), 0.95–1.05 (2H, m), 1.37(3H, d, J=6.4 Hz), 2.60–2.70(1H, m), 3.48(3H, s), 4.10–4.42(3H, m), 7.43–7.73(4H, m), 8.14(1H, s), 9.25 (1H, d, J=7.6 Hz)

FAB–MS m/z: 391(M+M)$^+$

Example 5
(See Reaction Scheme 2)

216.5 mg of ethyl 8-chloro-1-cyclopropyl-9-methyl-4-oxo-4H-quinolizine-3-carboxylate (1) was suspended in 2.2 ml of toluene, and 1.1 ml of ethanol, 0.55 ml of 2M sodium carbonate solution, 287.0 mg of 2-tritylisoindoline-5-boric acid (3) and 15.0 mg of bis(triphenylphosphin)paradium (II) chloride were added thereto, and thereafter, under an argon atmosphere, the resulting mixture was heated under reflux for 4.5 hours. Ethyl acetate was added to the reaction solution and the organic layer was separated and rinsed with water, and thereafter, dried over anhydrous sodium sulfate and the solvent was distilled off under reduced pressure. The resulting residue was purified directly by silica gel column chromatography (eluent; chloroform:ethyl acetate=6:1) to obtain 324.3 mg of ethyl 1-cyclopropyl-9-methyl-8-(2-tritylisoindoline-5-yl)-4-oxo-4H-quinolizine-3-carboxylate (I).

$^1$H-NMR(CDCl$_3$) δ:0.75(2H, m), 1.00(2H, m), 1.43(3H, t, J=7.1 Hz), 2.3(1H, m), 2.78 (3H, s), 4.02(4H, s), 4.42(2H, q, J=7.1 Hz), 7.02–7.63(19H, m), 8.40(1H, s), 9.43(1H, d, J=7.6 Hz)

Example 6

8.3 ml of ethanol, 2.8 ml of THF and 1.5 ml of 1N hydrochloric acid were added to 275.4 mg of ethyl 1-cyclopropyl-9-methyl-8-(2-tritylisoindoline-5-yl)-4-oxo-4H-quinolizine-3-carboxylate (I) and the resulting mixture was stirred at 50° C. for 2 hours. The solvent was distilled off under reduced pressure and water was added to the resulting residue and the resulting residue was washed with ethyl acetate, and thereafter, the resulting water layer was concentrated under reduced pressure. 30 ml of water, 10 ml of ethanol and 5 ml of 1N sodium hydroxide were added to the resulting residue and the resulting mixture was stirred at 50° C. for 3.5 hours. The reaction solution was concentrated under reduced pressure, and thereafter, dissolved in 4 ml of water and neutralized with 1N hydrochloric acid. The precipitated crystal was separated by filtering to obtain 120.0 mg of 1-cyclopropyl-9-methyl-8-(isoindoline-5-yl)-4-oxo-4H-quinolizine-3-carboxylic acid.

$^1$H-NMR(DMSO-d$_6$) δ: 0.75–0.80(2H, m), 1.05–1.15 (2H, m), 2.40–2.55(1H, m), 2.86(3H, s), 4.17(4H, s), 7.36–7.55(4H, m), 8.26(1H, s), 9.31(1H, d, J=7.6 Hz)

FAB–MS m/z: 361(M+H)$^+$

Reference Example 19
(See Reaction Scheme 3)

100.96 g of 2-acetylbenzoic acid (3-1) was dissolved in 500 ml of aqueous solution of 41.37 g of potassium hydroxide, to which 20.35 g of sodium boron hydride was added little by little at a room temperature. The resulting mixture was stirred at a room temperature for 2 days, and thereafter, the resulting mixture was adjusted to pH 1 with concentrated hydrochloric acid and extracted with chloroform. The resulting organic layer was dried over anhydrous sodium sulfate, and thereafter, the solvent was distilled off under reduced pressure. The resulting residue was purified by distilling under reduced pressure (117–121° C./3–5 mmHg) to obtain 86.45 g of 3-methylphtalide (3-2).

$^1$H-NMR(CDCl$_3$) δ: 1.64(3H, dd, J=1.2 Hz, 6.6 Hz), 5.58(1H, q, J=6.6 Hz), 7.45–7.90(4H, m)

Reference Example 20

66.40 g of 3-methylphtalide (3-2) was dissolved in 250 ml of fuming sulfuric acid, and under cooling with ice, 250 ml of concentrated sulfuric acid was dropped thereto, and thereafter, the resulting mixture was stirred at a room temperature for 15 hours. The reaction solution was poured into water and the precipitated crystal was separated by filtrating to obtain 73.91 g of 3-methyl-6-nitrophthalide (3-3).

$^1$H-NMR(CDCl$_3$) δ: 1.72(3H, d, J=6.8 Hz), 5.70(1H, q, J=6.8 Hz), 7.67(1H, d, J=8.5 Hz), 8.57(1H, dd, J=2.0 Hz, 8.5 Hz), 8.73(1H, d, J=2.0 Hz)

Reference Example 21

78.00 g of 3-methyl-6-nitrophthalide (3-3) was dissolved in 1.2 l of ethanol and 4.0 g of 5% palladium carbon was added thereto, and under a hydrogen atmosphere, the resulting mixture was stirred at a room temperature for 5 hours. The catalyst was filtered off, and thereafter, the filtrate was concentrated under reduced pressure, and the precipitated crystal was purified by recrystallizing (ethanol:water) to obtain 58.21 g of 6-amino-3-methylphtalide (3-4).

$^1$H-NMR(CDCl$_3$) δ: 1.58(3H, d, J=6.6 Hz), 3.95(2H, brs), 5.47(1H, q, J=6.6 Hz), 6.97(1H, dd, J=2.2 Hz, 8.1 Hz), 7.10(1H, d, J=2.2 Hz), 7.18(1H, d, J=8.1 Hz)

Reference Example 22

58.25 g of 6-amino-3-methylphtalide (3-4) was dissolved in 1.5 l of 4.7% hydrobromic acid and 405.60 g of copper (II) bromide was added thereto, and under cooling with ice, 400 ml of aqueous solution of 41.92 g of sodium nitrite was dropped thereto. The resulting mixture was stirred at the same temperature for 2 hours and then stirred at a room temperature for 15 hours, and thereafter, extracted with chloroform. The resulting organic layer was washed with saturated sodium bicarbonate solution and saturated salt water in order, and dried over anhydrous magnesium sulfate, and thereafter, the solvent was distilled off under reduced pressure, the resulting residue was purified by silica gel column chromatography (eluent; hexane:ethyl acetate=3:1) to obtain 71.56 g of 6-bromo-3-methylphtalide (3-5).

$^1$H-NMR(CDCl$_3$) δ: 1.64(3H, d, J=6.6 Hz), 5.54(1H, q, J=6.6 Hz), 7.33(1H, d, J=8.1 Hz), 7.80 (1H, dd, J=1.7 Hz, 8.1 Hz), 8.02(1H, d, J=1.7 Hz)

Reference Example 23

18.30 g of lithium aluminium hydroxide was suspended in 1.0 l of THF, to which 300 ml of THF solution of 36.44 g of 6-bromo-3-methylphtalide (3-5) was dropped at −30° C. and the resulting mixture was stirred at the same temperature for 2 hours. After the reaction was completed, 76 ml of water and 19 ml of 15% sodium hydroxide solution were added thereto, and the resulting residue was separated by filtering and the filtrate was concentrated under reduced pressure. Ethyl acetate was added to the resulting residue, which was washed with saturated salt water and dried over anhydrous magnesium sulfate, and thereafter, the solvent was distilled off under reduced pressure to obtain 36.84 g of 1-bromo-4-(1-hydroxyethyl)-3-hydroxymethylbenzene (3-6).

$^1$H-NMR(CDCl$_3$) δ: 1.48(3H, d, J=6.3 Hz), 3.52–3.61 (2H, m), 4.48–5.02(3H, m), 7.27–7.44 (3H, m)

Reference Example 24

36.84 g of 1-bromo-4-(1-hydroxyethyl)-3-hydroxymethylbenzene (3-6) was dissolved in 500 ml of diethyl ether, and under cooling with ice, 71.06 ml of phosphorus tribromide was dropped thereto, and thereafter, the resulting mixture was stirred at a room temperature for 24 hours. The reaction solution was poured into ice water and neutralized with sodium bicarbonate solution, and thereafter, extracted with ethyl acetate. The resulting organic layer was dried over anhydrous magnesium sulfate and the solvent was distilled off under reduced pressure to obtain 50.52 g of 1-bromo-4-(1-bromoethyl)-3-bromomethylbenzene (3-7).

$^1$H-NMR(CDCl$_3$) δ:2.07(3H, d, J=6.8 Hz), 4.39(1H, d, J=10.7 Hz), 4.70(1H, d, J=10.7 Hz), 5.51(1H, q, J=6.8 Hz), 7.45–7.49(3H, m)

Reference Example 25

3.97 g of about 60% sodium hydride was suspended in 70 ml of DMF, and 50 ml of DMF solution of 8.49 g of p-toluene sulfonamide in was added thereto, and the resulting mixture was stirred at 60° C. for 1 hour, and 50 ml of DMF solution of 17.70 g of 1-bromo-4-(1-bromoethyl)-3-bromomethylbenzene (3-7) was dropped thereto, which was stirred at the same temperature for 2 hours. The reaction solution was poured into ice water and extracted with chloroform and the resulting organic layer was dried over anhydrous magnesium sulfate, and thereafter, the solvent was distilled off under reduced pressure and the resulting residue was purified by chromatopraphy (eluent; hexane:chloroform=1:1) to obtain 14.13 g of 5-bromo-1-methyl-2-(p-toluene sulfonyl)isoindoline (3-8).

$^1$H-NMR(CDCl$_3$) δ: 1.64(3H, d, J=6.3 Hz), 2.39(3H, s), 4.51–4.89(3H, m), 6.96–7.75(7H, m)

Reference Example 26

67.46 g of 5-bromo-1-methyl-2-(p-toluene sulfonyl) isoindoline (3-8) was suspended in 325 ml of 47% hydrobromic acid and 48 ml of phenol and 197 ml of propionic acid were added thereto and the resulting mixture was heated under reflux for 4 hours. After the reaction was completed, the reaction mixture was adjusted to be alkaline with 8N sodium hydride solution and extracted with chloroform and the resulting organic layer was dried over anhydrous magnesium sulfate. The solvent was distilled off under reduced pressure and the resulting residue was purified by silica gel chromatopraphy (eluent; chloroform:methanol=19:1) to obtain 35.03 g of 5-bromo-1-methylisoindoline.

1H-NMR(CDCl$_3$) δ: 1.42(3H, d, J=6.6 Hz), 3.07(1H, brs), 4.13(1H, d, J=14.4 Hz), 4.22(1H, d, J=14.4 Hz), 4.39(1H, q, J=6.6 Hz), 7.03–7.36(3H, m)

Reference Example 27

20.00 g of 5-bromo-1-methylisoindoline was dissolved in 100 ml of THF, and 38.80 g of (N-benzyloxycarbonyl)-(L)- phenylalanine, 28.90 g of 1-hydroxybenzotriazol hydrate and 29.5 ml of N,N'-diisopropylcarbodiimide were added thereto and the resulting mixture was stirred at room temperature for 15 hours. The reaction solution was poured into ice water and adjusted to pH 1 with concentrated hydrochloric acid, and thereafter, extracted with diethylether and the resulting organic layer was dried over anhydrous magnesium sulfate. The solvent was distilled off under reduced pressure and the resulting residue was purified by silica gel chromatopraphy (eluent; hexane:diethyl ether=3:2) to obtain 17.42 g of 2-[(N-benzyloxycarbonyl)-(L)-phenylalanine]-5-bromo-1-methylisoindoline (3-9).

$^1$H-NMR(CDCl$_3$) δ: 1.33(3H, d, J=6.4 Hz), 2.96–3.13 (2H, m), 3.84–3.88(1H, m), 4.54–5.68 (6H, m), 7.01–7.38 (13H, m)

Reference Example 28

2.00 g of 2-[(N-benzyloxycarbonyl)-(L)-phenylalanine]-5-bromo-1-methylisoindoline (3-9) was suspendend in 50 ml of 47% hydrobromic acid, and in a closed tube, the resulting mixture was stirred at 120° C. for 60 hours. After completing the reaction, the resulting mixture was concentrated under reduced pressure, adjusted to be alkaline with 8N sodium hydroxide solution and extracted with chloroform and then the resulting organic layer was dried over anhydrous magnesium sulfate. The solvent was distilled off under reduced pressure and the resulting residue was dissolved in 2.0 ml of dichloromethane, and 351 mg of triethylamine was added thereto and 2.8 ml of dichloromethane solution of 920 mg of trithylchloride was dropped thereto and the resulting mixture was stirred at a room temperature for 16 hours. After the reaction was completed, water was added thereto and the resulting organic layer was separated and then washed with water, and thereafter, dried over anhydrous magnesium sulfate. The solvent was distilled off under reduced pressure and the resulting residue was purified by active alumina column chromatography (eluent; hexane:ethyl acetate=19:1) to obtain 1.16 g of (+)-5-bromo-1-methyl-2-trithylisoindoline (4).

$^1$H-NMR(CDCl$_3$) δ: 1.37(3H, d, J=6.6 Hz), 3.98–4.48 (3H, m), 6.56–7.53(18H, m) [α]$_D^{20}$=78° (c=1.0 CHCl$_3$)

Reference Example 29

335 mg of (+)-5-bromo-1-methyl-2-trithylisoindoline (4) was dissolved in 3.0 ml of THF, and under an argon atmosphere, 0.53 ml of n-buthyl lithium (n-hexane solution; 1.53 mol/l) was dropped thereto and the resulting mixture was stirred at the same temperature for 1 hour. 0.21 ml of triisopropyl borate was dropped to the mixture, which was stirred at the same temperature for 2 hours. The reaction solution was poured into ice water and neutralized with 1N hydrochloric acid, and thereafter, extracted with ethyl acetate and the resulting organic layer was dried over anhydrous magnesium sulfate, the solvent was distilled off under reduced pressure, and the resulting residue was purified by silica gel column chromatography (eluent; chroloform:ethyl acetate=3:1) to obtain 152 mg of (+)-1-methyl-2-trithylisoindoline-5-boric acid (3).

$^1$H-NMR(CDCl$_3$) δ: 1.40(3H, d, J=6.6 Hz), 3.99–4.58 (3H, m), 6.74–7.66(18H, m)

Example 7
(See Reaction Scheme 2) p 798.8 mg of ethyl 8-chloro-1-cyclopropyl-9-methoxy-4-oxo-4H-quinolizine-3-carboxylate (XIII) was suspended in 8 ml of toluene, and 4 ml of ethanol, 2 ml of 2M sodium carbonate aqueous solution, 1.06 g of 2-tritylisoindoline-5-boric acid and 80 mg of bis(triphenylphosphin)paradium (II) chloride were added thereto, and thereafter, under an argon atmosphere, the resulting mixture was heated under reflux for 4.5 hours. Ethyl acetate was added to the reaction solution and the organic layer was separated and rinsed with water, and thereafter, dried over anhydrous sodium sulfate and the solvent was distilled off under reduced pressure. The resulting residue was purified by silica gel column chromatography (eluent; chloroform:ethyl acetate=5:1) to obtain 1.21 g of ethyl 1-cyclopropyl-9-methoxy-8-(2 -tritylisoindoline-5-yl)-4-oxo-4H-quinolizine-3-carboxylate (I).

$^1$H-NMR(CDCl$_3$) δ: 0.72–0.76(2H, m), 0.95–0.97(2H, m), 1.43(3H, t, J=7.1 Hz), 2.51–2.56(1H, m), 3.45(3H, s), 4.02(4H, s), 4.40(2H, q, J=7.1 Hz), 7.12–7.62 (19H, m), 8.24(1H, s), 9.35(1H, d, J=7.6 Hz)

Example 8

12 ml of THF, 36 ml of ethanol, and 6 ml of 1N hydrochloric acid were added to 1.21 g of ethyl 1-cyclopropyl-9-methoxy-8-(2-methylisoindoline-5-yl)-4-oxo-4H-quinolizine-3-carboxylate (I), which was stirred at 50° C. for 1.5 hours. The solvent was distilled off under reduced pressure and water was added to the resulting residue, which was washed with ethyl acetate, and thereafter, the resulting water layer was concentrated under reduced pressure. 20 ml of ethanol and 6 ml of 1N sodium hydroxide were added to the residue, which was stirred at 50° C. for 2 hours. The reaction solution was concentrated under reduced pressure, and thereafter, dissolved in 10 ml of water and neutralized with 1N hydrochloric acid. The precipitated crystal was separated by filtering to obtain 515 mg of 1-cyclopropyl-9-methoxy-8-(isoindoline-5-yl)-4-oxo-4H-quinolizine-3-carboxylic acid (I).

$^1$H-NMR(CF$_3$COOD) δ: 1.15–1.16(2H, m), 1.46–1.48 (2H, m), 3.10–3.11(1H, m), 3.84(3H, s), 5.16–5.17(4H, m), 7.84(1H, d, J=8.0 Hz), 8.06–8.10(2H, m), 8.16(1H, d, J=7.3 Hz), 8.47(1H, brs), 8.71(1H, s), 9.50(1H, d, J=7.3 Hz)

FAB–MS m/z: 377(M+H)$^+$

Reference Example 30
(See Reaction Scheme 1)

76.38 g of 4-chloro-3-difluoromethoxy-2-methylpyridine (XIX) was dissolved in 2500 ml of anhydrous dichloromethane, to which 93.62 g of 3-chloro-perbenzoic acid was added under cooling with ice, and the resulting mixture was stirred at 5° C. for 12 hours. The resulting organic layer was washed with 5% sodium carbonate solution, and thereafter, dried over anhydrous sodium sulfate. The solvent was distilled off under reduced pressure to obtain 77.97 g of 4-chloro-3-difloromethoxy-2-methylpyridine N-oxide (VI).

$^1$H-NMR(CDCl$_3$) δ: 2.55(3H, s), 6.59(1H, t, J=73.0 Hz), 7.23(1H, d, J=7.1 Hz), 8.17(1H, d, J=7.1 Hz)

Reference Example 31

744 ml of acetic anhydride was added to 77.97 g of 4-chloro-3-difloromethoxy-2-methylpyridine N-oxide (VI), which was heated at 100° C. for 4 hour. The solvent was distilled off under reduced pressure and 2N sodium hydroxide was added thereto to adjust to pH 11 and the resulting mixture was heated at 100° C. for 1 hour. The resulting mixture was extracted with chloroform and the resulting organic layer was washed with saturated salt water and dried over anhydrous sodium sulfate and the solvent was distilled off under reduced pressure. The resulting residue was purified by silica gel column chromatography (eluent; chloroform:ethyl acetate=5:1) to obtain 23.11 g of 4-chloro-3-difluoromethoxy-2-hydroxymethylpyridine (VII).

$^1$H-NMR(CDCl$_3$) δ: 3.94(1H, t, J=5.1 Hz), 4.84(2H, d, J=5.1 Hz), 6.60(1H, t, J=73.5 Hz), 7.38(1H, d, J=5.4 Hz), 8.40(1H, d, J=5.4 Hz)

Reference Example 32

12.5 ml of oxalyl chloride was dissolved in 262 ml of anhydrous dichloromethane, under cooling at −78° C., 131 ml of anhydrous dichloromethane solution of 10.9 ml of anhydrous dimethylsulfoxide was dropped thereto. The resulting mixture was stirred at −78° C. for 40 minutes, and thereafter, 306 ml of anhydrous dichloromethane solution of 23.11 g of 4-chloro-3-difluoromethoxy-2-hydroxymethylpyridine (VII) was dropped thereto. The resulting mixture was stirred at −78° C. for 30 minutes, and thereafter, the reaction temperature was elevated to −45° C., and the resulting mixture was stirred at the same temperature for 1 hour, and thereafter, 76.9 ml of triethylamine was dropped thereto and the temperature of the resulting mixture was elevated to a room temperature. Water was added to the resulting mixture, which was extracted with chloroform, and the resulting organic layer was washed with water and saturated salt water, and thereafter, dried over anhydrous sodium sulfate, and the solvent was distilled off under reduced pressure. The resulting residue was purified by silica gel column chromatography (eluent; chloroform:ethyl acetate=5:1) to obtain 18.79 g (4-chloro-3-difloromethoxypyridine)-2-carbardehyde (VIII).

$^1$H-NMR(CDCl$_3$) δ: 6.77(1H, t, J=74.2 Hz), 7.67(1H, d, J=5.1 Hz), 8.62(1H, d, J=5.1 Hz), 10.18(1H, s)

Reference Example 33

120 ml of THF solution of 18.79 g of (4-chloro-3-difluoromethoxypyridine)-2-carbardehyde (VIII) was dropped to 144 ml of THF solution of magnesium cyclopropyl bromide which was prepared from 10.9 ml of cyclopropyl bromide and 3.30 g of magnesium. The resulting mixture was stirred at a room temperature for 12 hours, and poured into saturated ammonium chloride and extracted with chloroform. The resulting organic layer was washed with saturated salt water and dried over anhydrous sodium sulfate and the solvent was distilled off under reduced pressure. The resulting residue was purified by silica gel column chromatography (eluent; chloroform:ethyl acetate=10:1) to obtain 12.38 g of (4-chloro-3-difluoromethoxy-2-pyridyl)cyclopropylmethane-1-ol (IX).

$^1$H-NMR(CDCl$_3$) δ: 0.44–0.62(4H, m), 1.18–1.26(1H, m), 3.79(1H, d, J=8.1 Hz), 4.70(1H, m), 6.61(1H, dd, J=75.7, 71.5 Hz), 7.37(1H, d, J=5.1 Hz), 8.39(1H, d, J=5.1 Hz)

Reference Example 34

6.44 ml of oxalyl chloride was dissolved in 150 ml of anhydrous dichloromethane, under cooling at −78° C., 75 ml of anhydrous dichloromethane solution of 5.64 ml of anhydrous dimethylsulfoxide was dropped. The resulting mixture was stirred at −78° C. for 40 minutes, and thereafter, 150 ml of anhydrous dichloromethane solution of 14.17 g of (4-chloro-3-difluoromethoxy-2-pyridyl)cyclopropylmethane-1-ol (IX) was dropped thereto. The resulting mixture was stirred at −78° C. for 30 minutes, and thereafter, the reaction temperature was elevated to −45° C., and the resulting mixture was stirred at the same temperature for 1 hour, and thereafter, 39.56 ml of triethylamine was dropped and the temperature of the resulting mixture was elevated to a room temperature. Water was added thereto and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; chloroform:ethyl acetate= 125:1) to obtain 12.57 g of (4-chloro-3-difluoromethoxy-2-pyridyl)cyclopropylketone (X).

$^1$H-NMR(CDCl$_3$) δ: 1.12–1.32(4H,m), 2.98–3.04(1H, m), 6.76(1H, t, J=75.0 Hz), 7.59(1H, d, J=5.1 Hz), 8.49(1H, d, J=5.1 Hz)

Reference Example 35

18.27 g of (methoxymethyl) triphenyl phosphonium chloride is suspended in 200 ml of anhydrous ether, 51.3 ml of phenyllithium (1.04 M) was dropped and the resulting mixture was stirred at a room temperature for 15 minutes. 145 ml of ether solution of 12.57 g of (4-chloro-3-difluoromethoxy-2-pyridyl)cyclopropylketone (X) was dropped to the mixture, which was stirred at a room temperature for 12 hours. The resulting residue was separated by filtering and washed with ether, and thereafter, the ether filtrate and ether used for washing were collected together and the collected solution was washed with water, and thereafter, dried over anhydrous sodium sulfate and the solvent was distilled off under reduced pressure. The resulting residue was purified by silica gel column chromatography (eluent; hexane:ethyl acetate=4:1) to obtain 1.66 g of 2-(4-chloro-3-difluomethoxy-2-pyridyl)-2-cyclopropyl-1-methoxyethene (XI).

$^1$H-NMR(CDCl$_3$)

δ1: 0.43–0.47(2H, m), 0.73–0.78(2H, m), 1.77–1.84(1H, m), 3.78(3H, s), 6.49(1H, t, J=77.5 Hz), 6.61(1H, d, J=1.2 Hz),7.23(1H, d, J=5.1 Hz), 8.29(1H, d, J=5.1 Hz)

δ2: 0.43–0.46(2H, m), 0.60–0.64(2H, m), 1.61–1.68(1H, m), 3.60(3H, s), 6.22(1H, d, J=1.0 Hz), 6.43(1H, t, J=74.2 Hz), 7.30(1H, d, J=4.9 Hz), 8.40(1H, d, J=4.9 Hz)

Reference Example 36

6.00 g of 2-(4-chloro-3-difluoromethoxy-2-pyridyl)-2-cyclopropyl-1-methoxyethene (XI) was dissolved in 60 ml of THF, to which 40 ml of dilute sulfuric acid was added, and the resulting mixture was concentrated at 50° C. under reduced pressure. The resulting mixture was poured into water and neutralized with saturated sodium bicarbonate solution, and thereafter, extracted with chloroform. The resulting organic layer was washed with saturated salt water, and thereafter, dried over anhydrous sodium sulfate and the solvent was distilled off under reduced pressure. The resulting residue was purified by silica gel column chromatography (eluent; hexane:ethyl acetate=4:1) to obtain 4.51 g of 2-(4-chloro-3-difluoromethoxy-2-pyridyl)-2-cyclopropylethanal (XII).

$^1$H-NMR(CDCl$_3$) δ: 0.27–0.86(4H, m), 1.50–1.59(1H, m), 3.37–3.40(1H, m), 6.53(1H, t, J=73.0 Hz), 7.36(1H, d, J=5.1 Hz), 8.45(1H, d, J=5.1 Hz), 9.98(1H, d, J=1.7 Hz)

Reference Example 37

4.30 g of 2-(4-chloro-3-difluoromethoxy-2-pyridyl)-2-cyclopropylethanal (XII) was dissolved in 120 ml of anhydrous ethanol, to which 4.0 ml of piperidine, 4.0 ml of acetic acid and 12.5 ml of diethylmalonate were added and heated at 100° C. for 5 hours. The solvent was distilled off under reduced pressure, and thereafter, the resulting mixture was diluted with ether and the resulting organic layer was washed with water and saturated salt water, and thereafter, dried over anhydrous sodium sulfate and the solvent was distilled off under reduced pressure. 110 ml of Dowtherm A was added to the resulting residue, which was heated at 240° C. for 30 minutes. The reaction solution was purified directly by silica gel column chromatography (eluent; hexane→hexane:ethyl acetate=1:1) to obtain 3.48 g of ethyl 8-chloro-1-cyclopropyl-9-difloromethoxy-4-oxo-4H-quinolizine-3-carboxylate (XIII).

$^1$H-NMR(CDCl$_3$) δ: 0.67–0.71(2H, m), 1.01–1.06(2H, m), 1.42(3H, t, J=7.3 Hz), 2.35–2.42 (1H, m), 4.42(2H, q, J=7.3 Hz), 6.69(1H, t, J=74.2 Hz), 7.09(1H, d, J=7.8 Hz), 8.35(1H, s), 9.30(1H, d, J=7.8 Hz)

Example 9

(See Reaction Scheme 1)

1.50 g of ethyl 8-chloro-1-cyclopropyl-9-difloromthoxy-4-oxo-4H-quinolizine-3-carboxylate (XIII) was suspended in 20.96 ml of toluene, to which were added 10.48 ml of ethanol, 5.24 ml of 2M sodium carbonate aqueous solution, 2.11 mg of (+)-1-methyl-2-tritylisoindoline-5-boric acid (3) and 147 mg of bis(triphenylphosphin)paradium (II) chloride, and thereafter, under an argon atmosphere, the resulting mixture was heated under reflux for 1 hour. Chloroform was added to the reaction solution and the resulting organic layer was separated and rinsed with water, and thereafter, dried over anhydrous sodium sulfate and the solvent was distilled off under reduced pressure. The resulting residue was purified by silica gel column chromatography (eluent; chloroform:ethyl acetate=9:1) to obtain 2.27 g of ethyl 1-cyclopropyl-9-difloromethoxy-8-((+)-1-methyl-2-tritylisoindoline-5-yl)-4-oxo-4H-quinolizine-3-carboxylate (I).

$^1$H-NMR(CDCl$_3$) δ: 0.68–0.73(2H, m), 0.99–1.05(2H, m), 1.42(3H, t, J=7.1 Hz), 1.48(3H, d, J=6.6 Hz), 2.41(1H, m), 4.10–4.66(5H, m), 5.65(1H, dd, J=74.0, 78.1 Hz), 6.92–7.58(19H, m),8.35(1H, s), 9.36(1H, d, J=7.6 Hz)

Example 10

68 ml of ethanol, 23 ml of THF and 11 ml of 1N hydrochloric acid were added to 2.26 g of ethyl 1-cyclopropyl-9-difluoromethoxy-8-((+)-1-methyl-2-tritylisoindoline-5-yl)-4-oxo-4H-quinolizine-3-carboxylate (I), which was stirred at 50° C. for 1 hour. The solvent was distilled off under reduced pressure and water was added to the resulting residue, which was washed with ethyl acetate, and thereafter, the resulting water layer was concentrated under reduced pressure. 30 ml of water, 30 ml of ethanol and 30 ml of 1N sodium hydroxide were added to the resulting residue, which was stirred at 50° C. for 1 hour. The reaction solution was concentrated under reduced pressure, and thereafter, dissolved in 200 ml of water and neutralized with 1N hydrochloric acid. The precipitated crystal was separated by filtering to obtain 899 mg of 1-cyclopropyl-9-difluoromethoxy-8-((+)-1-methylisoindoline-5-yl)-4-oxo-4H-quinolizine-3-carboxylic acid (I).

$^1$H-NMR(CF$_3$COOD) δ: 1.10–1.14(2H, m), 1.47–1.52 (2H, m), 2.04(3H, d, J=6.8 Hz), 2.90–2.97(1H, m), 5.05–5.52(3H, m), 6.46(1H, t, J=71.8 Hz), 7.77–8.19(4H, m), 8.83(1H, s), 9.61–9.63(1H, m)

FAB–MS m/z: 427(M+H)$^+$

Example 11

(See Reaction Scheme 2)

787 mg of ethyl 8-chloro-1-cyclopropyl-9-difloromethoxy-4-oxo-4H-quinolizine-3-carboxylate (XIII) was suspended in 8 ml of toluene to which were added 4 ml of ethanol, 2 ml of 2M sodium carbonate solution, 1.07 g of 2-tritylisoindoline-5-boric acid and 80 mg of bis (triphenylphosphin)paradium (II) chloride, and thereafter, under an argon atmosphere, the resulting mixture was heated under reflux for 4 hours. Ethyl acetate was added to the reaction solution and the organic layer was seperated and rinsed with water, and thereafter, dried over anhydrous sodium sulfate and the solvent was distilled off under reduced pressure. The resulting residue was purified by silica gel column chromatography (eluent; chloroform:ethyl acetate=4:1) to obtain 1.07 g of ethyl 1-cyclopropyl-9-difloromethoxy-8-(2-tritylisoindoline-5-yl)-4-oxo-4H-quinolizine-3-carboxylate (I).

$^1$H-NMR(CDCl$_3$) δ: 0.70–0.74(2H, m), 0.95–1.05(2H, m), 1.43(3H, t, J=7.1 Hz), 2.41–2.48(1H, m), 4.04(4H, s), 4.42(2H, q, J=7.1 Hz), 6.00(1H, t, J=75 Hz), 7.10–7.62(19H, m), 8.36(1H, s), 9.40(1H, d, J=7.6 Hz)

Example 12

7.6 ml of THF, 2.5 ml of ethanol, and 1.3 ml of 1N hydrochloric acid were added to 930 mg of ethyl 1-cyclopropyl-9-difloromethoxy-8-(2-tritylisoindoline-5-yl)-4-oxo-4H-quinolizine-3-carboxylate (I), which was stirred at a room temperature for 90 minutes. The solvent was distilled off under reduced pressure and water was added to the resulting residue, which was washed with ethyl acetate, and thereafter, the resulting water layer was concentrated under reduced pressure. 10 ml of methanol and 5 ml of 1N sodium hydroxide were added to the resulting residue, which was stirred at 50° C. for 2 hours. The reaction solution was concentrated under reduced pressure, and thereafter, dissolved in 10 ml of water and neutralized with 1N hydrochloric acid. The precipitated crystal was separated by filtering to obtain 388 mg of 1-cyclopropyl-9-difloromethoxy-8-(isoindoline-5-yl)-4-oxo-4H-quinolizine-3-carboxylic acid (I).

$^1$H-NMR(CF$_3$COOD) δ: 1.25–1.27(2H, m), 1.62–1.66 (2H, m), 3.07–3.10(1H, m), 5.29–5.31(4H, m), 6.60(1H, t, J=72 Hz), 7.97 (1H, d, J=8.0 Hz), 8.15–8.19(2H, m), 8.33 (1H, dd, J=7.6 Hz), 8.98(1H, s), 9.76(1H, d, J=7.6 Hz)

FAB–MS m/z: 413(M+H)$^+$

Reference Example 38

(See Reaction Scheme 4)

The mixture of 90.60 g of 2,3-dimethylnitrobenzene (3-10) and 1.20 g of iron powder was heated at 75° C., to which 115.00 g of bromine was dropped with stirring, and then the resulting mixture was stirred at the same temperature for 4 hours. The reaction solution was poured into ice water, and extracted with ethyl acetate, and the resulting organic layer was washed with sodium thiosulfate solution and saturated salt water in order, and dried over anhydrous magnesium sulfate. The solvent was distilled off under reduced pressure and 400 ml of methanol and 400 ml of concentrated hydrochloric acid were added to the resulting residue, to which 100 g of iron powder was added in a divided form, and thereafter, the resulting mixture was stirred at 70° C. for 30 minutes. The reaction solution was poured into ice water, and the resulting mixture was alkaline with sodium bicarbonate, and thereafter, extracted with ethyl acetate and the resulting organic layer was dried over anhydrous magnesium sulfate. The solvent was removed under reduced pressure, and the resulting residue was purified by silica gel column chromatography (eluent;

hexane:ethylacetate=9:1) to obtain 48.82 g of 5-bromo-2,3-dimethylaniline (3-11).

¹H-NMR(CDCl₃) δ: 2.00(3H, s), 2.22(3H, s), 3.61(2H, bs), 6.69(1H, d, J=2.0 Hz), 6.75(1H, d, J=2.0 Hz)

Reference Example 39

4.00 g of 5-bromo-2,3-dimethylaniline (3-11) was dissolved in 50 ml of hydrogen fluoride-pyridine, to which under cooling with ice, 5.00 ml of an aqueous solution of 2.10 g of sodium nitrite was dropped. The resulting mixture was stirred at the same temperature for 30 minutes and further stirred at a room temperature for 1 hour, and thereafter, stirred at 85° C. for 1 hour. The reaction solution was poured into ice water and extracted with ethyl acetate and the resulting organic layer was washed with sodium bicarbonate solution, and thereafter, the resulting organic layer was dried over anhydrous magnesium sulfate. The solvent was removed under reduced pressure and the resulting residue was purified by silica gel column chromatography (eluent; hexane:ethyl acetate=10:1) to obtain 2.92 g of 5-bromo-1-fluoro-2,3-dimethylbenzene (3-12).

¹H-NMR(CDCl₃) δ: 2.11(3H, d, J=2.2 Hz), 2.50(3H, s), 7.02–7.08(2H, m)

Reference Example 40

2.92 g of 5-bromo-1-fluoro-2,3-mdimethylbenzene (3-12) was dissolved in 30 ml of carbon tetrachloride, to which were added 5.63 g of N-bromosuccinimide and 0.12 g of α,α'-azobis(isobutylnitrile), and the resulting mixture was heated under a hydrogen atmosphere under reflux for 3 hours. The reaction solution was poured into water, and extracted with ethyl acetate, and the resulting organic layer was dried over anhydrous magnesium sulfate, and thereafter, the solvent was removed under reduced pressure, and the resulting residue was purified by silica gel column chromatography (eluent; hexane:ethyl acetate=14:1) to obtain 5.02 g of 5-bromo-1,2-bis(bromomethyl)-3-fluorobenzene (3-13).

¹H-NMR(CDCl₃) δ: 4.54(2H, s), 4.61(2H, s), 7.22–7.34 (2H, m)

Reference Example 41

1.17 g of about 60% sodium hydride was suspended in 30 ml of DMF, to which was added 15 ml of DMF solution of 2.50 g of p-toluene sulfonamide, and the resulting mixture was stirred at 60° C. for 1 hour. 15 ml of DMF solution of 5.02 g of 5-bromo-1,2-bis(bromomethyl)-3-fluorobenzene (3-13) was dropped thereto and the resulting mixture was stirred at the same temperature for 1 hour. The reaction solution was poured into ice water and the precipitated crystal was separated by filtering to obtain 5.10 g of 6-bromo-4-fluoro-2-(p-toluensulfonyl)isoindoline (3–14).

¹H-NMR(CDCl₃) δ: 2.42(3H, s), 4.59–4.61(4H, m), 7.09–7.77(6H, m)

Reference Example 42

5.10 g of 6-bromo-4-fluoro-2-p-toluensulfonyl)isoindoline (3-14) was suspended in 50 ml of 47% hydrobromic acid, to which were added 3.89 g of phenol and 12.41 g of acetic acid and the resulting mixture was heated under reflux for 4 hours. After the reaction was completed, the resulting mixture was concentrated under reduced pressure and water was added thereto and the resulting mixture was washed with ethyl acetate, and thereafter, the resulting water layer was separated and concentrated under reduced pressure and dried to 2.38 g of 6-bromo-4-fluoroisoindoline hydrobromate (3-15).

¹H-NMR(CD₃OD) δ: 4.66–4.69(4H, m), 7.39–7.49(2H, m)

Reference Example 43

2.38 g of 6-bromo-4-fluoroisoindoline hydrobromate (3-15) was dissolved in 50 ml of dichloromethane, to which was added 2.43 g of triethylamine, and then to which 50 ml of dichloromethane solution of 2.68 g of trithylchloride was dropped, and the resulting mixture was stirred at a room temperature for 2 hours. After the reaction was completed, water was added thereto and the resulting organic layer was separated and rinsed with water, and thereafter, dried over anhydrous magnesium sulfate. The solvent was distilled off under reduced pressure, and the resulting residue was purified by active alumina column chromatography (eluent; hexane) to obtain 2.13 g of 6-bromo-4-floro-2-tritylisoindoline (3-16).

¹H-NMR(CDCl₃) δ: 3.89–4.01(4H, m), 6.95–7.57(17H, m)

Reference Example 44

2.13 g of 6-bromo-4-floro-2-tritylisoindoline (3-16) was dissolved in 50 ml of THF, to which under an argon atmosphere, 3.87 ml of n-butyllithium (n-hexane solution; 1.50 mol/l) was dropped at −78° C. and the resulting mixture was stirred at the same temperature for 30 minutes. 1.18 ml of triisopropyl borate was dropped thereto and then the resulting mixture was stirred at the same temperature for 1 hour. The reaction solution was poured into ice water, and neutralized with saturated ammonium chloride solution, and thereafter, extracted with ethyl acetate and the resulting organic layer was dried over anhydrous magnesium sulfate. The solvent was distilled off under reduced pressure, and the resulting residue was purified by silica gel column chromatography (eluent; chloroform:ethyl acetate=4:1) to obtain 307 mg of 4-fluoro-2-tritylisoindoline-6-boric acid (3).

¹H-NMR(CDCl₃) δ: 3.69–4.15(4H, m), 7.10–7.61(17H, m)

Example 13
(See Reaction Scheme 2)

108 mg of ethyl 8-chloro-1-cyclopropyl-9-methyl-4-oxo-4H-quinolizine-3-carboxylate (XIII) was suspended in 1.48 ml of toluene, to which were added 0.74 ml of ethanol, 0.37 ml of 2M sodium carbonate solution, 150 mg of 4-fluoro-2-tritylisoindoline-6-boric acid (3) and 12 mg of bis(triphenylphosphin)paradium (II) chloride, and thereafter, under an argon atmosphere, the resulting mixture was heated under reflux for 1 hour. Chloroform was added to the reaction solution and the resulting organic layer was separated and rinsed with water, and thereafter, dried over anhydrous sodium sulfate and the solvent was distilled off under reduced pressure. The resulting residue was purified by silica gel column chromatography (eluent; chloroform:ethyl acetate=9:1) to obtain 150 mg of ethyl cyclopropyl-9-methyl-8-(4-fluoro-2-trithylisoindoline-6-yl)-4-oxo-4H-quinolizine-3-carboxylate (I).

¹H-NMR(CDCl₃) δ: 0.74–0.78(2H, m), 1.00–1.04(2H, m), 1.40–1.44(3H, m), 2.30–2.39(1H, m), 2.77–2.89(3H, m), 4.08–4.45(4H, m), 6.56–7.62(20H, m), 8.40–8.41(1H, m), 9.41–9.45(1H, m)

Example 14

4.5 ml of ethanol, 1.5 ml of THF and 0.75 ml of 1N hydrochloric acid were added to 150 mg of ethyl 1-cyclopropyl-9-methyl-8-(4-fluoro-2-tritylisoindoline-6-yl)-4-oxo-4H-quinolizine-3-carboxylate (I), which was stirred at 50° C. for 2 hours. The solvent was distilled off under reduced pressure and water was added to the resulting residue, which was washed with ethyl acetate, and thereafter, the resulting water layer was concentrated under reduced pressure. 5 ml of water, 5 ml of ethanol and 5 ml of 1N sodium hydroxide were added to the residue and the resulting mixture was stirred at 50° C. for 1 hour. The reaction solution was concentrated under reduced pressure, and thereafter, dissolved in 2 ml of water and neutralized with 1N hydrochloric acid. The precipitated crystal was separated by filtering to obtain 28.4 mg of 1-cyclopropyl-8-(4-fluoroisoindoline-6-yl)-9-methyl-4-oxo-4H-quinolizine-3-carboxylic acid.

$^1$H-NMR(CF$_3$COOD) δ: 1.16–1.17(2H, m), 1.51–1.53 (2H, m), 2.74–2.83(1H, m), 3.26(3H, s), 5.14–5.22(4H, m), 7.41–7.43(1H, m), 7.49(1H, s), 7.99(1H, d, J=7.3 Hz), 8.87(1H, s), 9.57(1H, d, J=7.3 Hz)

FAB–MS m/z: 379(M+H)$^+$

Reference Example 45
(See Reaction Scheme 5)

10.00 g of 5-bromo-2,3-dimethylaniline (3-11) was dissolved in a mixed solution of 50 ml of 25% sulfuric acid and 50 ml of toluene, and under cooling with ice, 20 ml of aqueous solution of 3.80 g of sodium nitrite was dropped thereto. The resulting mixture was stirred at the same temperature for 1 hour, and then stirred at 100° C. for 1 hour, and thereafter, the reaction solution was poured into ice water and extracted with ethyl acetate and the resulting organic layer was washed with saturated salt water, and thereafter, the resulting organic layer was dried over anhydrous magnesium sulfate. The solvent was distilled off under reduced pressure, and the resulting residue was purified by silica gel column chromatography (eluent; hexane:ethyl acetate=9:1) to obtain 5.49 g of 5-bromo-2,3-dimethylphenol (3-17).

$^1$H-NMR(CDCl$_3$) δ: 2.09(3H, s), 2.23(3H, s), 4.77(1H, s), 6.79(1H, d, J=1.7 Hz), 6.90(1H, d, J=1.7 Hz)

Reference Example 46

5.49 g of 5-bromo-2,3-dimethylphenol (3-17) was dissolved in 100 ml of DMF, to which were added 6.80 g of methyl iodide and 11.32 g of potassium carbonate, and the resulting mixture was stirred at 90° C. for 2 hours. The reaction solution was poured into water, and extracted with ethyl acetate and the resulting organic layer was washed with saturated salt water, and thereafter, the resulting organic layer was dried over anhydrous magnesium sulfate. The solvent was removed under reduced pressure, and the resulting residue was purified by silica gel column chromatography (eluent; hexane:ethyl acetate=9:1) to obtain 5.35 g of 5-bromo-1-methoxy-2,3-dimethylbenzene (3-18).

$^1$H-NMR(CDCl$_3$) δ: 2.07(3H, s), 2.23(3H, s), 3.79(3H, s), 6.83(1H, s), 6.93(1H, s)

Reference Example 47

2.80 g of 5-bromo-1-methoxy-2,3-dimethylbenzene (3-18) was dissolved in 30 ml of carbon tetrachloride, to which were added 5.10 g of N-bromosuccinimide and 107 mg of α,α'-azobis(isobutyronitrile), and the resulting mixture was heated under reflux for 3 hours. The reaction solution was poured into water, and extracted with ethyl acetate, and the resulting organic layer was washed with saturated salt water and dried over anhydrous magnesium sulfate. The solvent was removed under reduced pressure, and the resulting residue was purified by silica gel column chromatography (eluent; hexane:ethyl acetate=6:1) to obtain 4.77 g of 5-bromo-1,2-bis(bromomethyl)-3-methoxybenzene (3-19).

$^1$H-NMR(CDCl$_3$) δ: 3.89(3H, s), 4.53(2H, s), 4.69(2H, s), 7.00(1H, d, J=1.7 Hz), 7.13(1H, d, J=1.7 Hz)

Reference Example 48

4.95 g of 5-bromo-1,2-bis(bromomethyl)-3-methoxybenzene (3-19) was dissolved in 150 ml of anhydrous DMF, to which 5.50 g of potassium carbonate and 4.30 g of tritylamine, and under an argon atmosphere, the resulting mixture was stirred at 90° C. for 8 hours. The reaction solution was poured into water, and extract with chloroform and the resulting organic layer was washed with saturated salt water, and thereafter, the resulting organic layer was dried over anhydrous magnesium sulfate. The solvent was distilled off under reduced pressure, and thereafter, the resulting residue was recrystallized with 2-propanol to obtain 3.35 g of 6-bromo-4-methoxy-2-tritylisoindoline (3-20).

$^1$H-NMR(CDCl$_3$) δ: 3.73(3H, s), 3.88–3.93(4H, m), 6.75 (1H, s), 6.83(1H, s), 7.13–7.57 (15H, m)

Reference Example 49

1.02 g of 6-bromo-4-methoxy-2-tritylisoindoline (3-20) was dissolved in 5 ml of THF, and under an argon atmosphere, 1.59 ml of n-butyllithium (n-hexane solution; 1.50 mol/l) was dropped thereto at −78° C. and the resulting mixture was stirred at the same temperature for 30 minutes. 0.6 ml of triisopropyl borate was dropped to the mixture which was stirred at the same temperature for 1 hour. The reaction solution was poured into ice water, and neutralized with acetic acid, and thereafter, extracted with ethyl acetate and dried over anhydrous magnesium sulfate. The solvent was distilled off under reduced pressure, and the resulting residue was purified by silica gel column chromatography (eluent; chloroform:ethyl acetate=4:1) to obtain 380 mg of 4-methoxy-2-trityl-isoindoline-6-boric acid (3).

Example 15
(See Reaction Scheme 2)

152.2 mg of ethyl 8-chloro-1-cyclopropyl-9-methoxy-4-oxo-4H-quinolizine-3-carboxylate (XIII) was suspended in 1.5 ml of toluene, to which were added 0.8 ml of ethanol, 0.4 ml of 2M sodium carbonate aqueous solution, 247.1 mg of 4-methoxy-2-tritylisoindoline-6-boric acid and 15 mg of bis(triphenylphosphin)paradium (II) chloride, and thereafter, under an argon atmosphere, the resulting mixture was heated under reflux for 4 hours. Ethyl acetate was added to the reaction solution and the resulting organic layer was separated and rinsed with water, and thereafter, dried over anhydrous sodium sulfate and the solvent was distilled off under reduced pressure. The resulting residue was purified by silica gel column chromatography (eluent; chloroform:ethyl acetate=6:1) to obtain 120 mg of ethyl 1-cyclopropyl-9-methoxy-8-(4-methoxy-2-tritylisoindoline-6-yl)-4-oxo-4H-quinolizine-3-carboxylate (I).

$^1$H-NMR(CDCl$_3$) δ: 0.74–0.75(2H, m), 0.95–0.98(2H, m), 1.43(3H, t, J=7.1 Hz), 2.57(1H, m), 3.47(3H, s), 3.81 (3H, s), 4.04(4H, m), 4.42(2H, q, J=7.1 Hz), 6.98–7.63(18H, m), 8.24(1H, s), 9.34(1H, d, J=7.3 Hz)

Example 16

3.6 ml of THF, 1.2 ml of ethanol, and 0.6 ml of 1N hydrochloric acid were added to 120 mg of ethyl 1-cyclopropyl-9-methoxy-8-(4-methoxy-2-tritylisoindoline-6-yl)-4-oxo-4H-quinolizine-3-carboxylate (I), which was stirred at 50° C. for 2 hours. The solvent was distilled off under reduced pressure and water was added to the resulting residue, which was washed with ethyl acetate, and thereafter, the resulting water layer was concentrated under reduced pressure. 2 ml of methanol and 0.5 ml of 1N sodium hydroxide were added to the resulting residue and the resulting mixture was stirred at 50° C. for 2 hours. The reaction solution was concentrated under reduced pressure, and thereafter, dissolved in 10 ml of water and neutralized with 1N hydrochloric acid. The precipitated crystal was separated by filtering to obtain 16.7 mg of 1-cyclopropyl-9-methoxy-8-(4-methoxyisoindoline-6-yl)-4-oxo-4H-quinolizine-3-carboxylic acid (I).

$^1$H-NMR(CF$_3$COOD) δ: 1.13–1.17(2H, m), 1.43–1.48 (2H, m), 3.10(1H, m), 3.88(3H, s), 4.16(3H, s), 5.10–5.15 (4H, m), 7.56(1H, s), 7.59(1H, s), 8.16(1H, d, J=7.3 Hz), 8.39(1H, brs), 8.71(1H, s), 9.48(1H, d, J=7.3 Hz)

FAB–MS m/z: 407(M+H)$^+$

Example 17

80.1 mg of ethyl 8-chloro-1-cyclopropyl-9-methyl-4-oxo-4H-quinolizine-3-carboxylate (XIII) was suspended in 0.8 ml of toluene, to which were added 0.4 ml of ethanol, 0.2 ml of 2M sodium carbonate solution, 130 mg of 4-methoxy-2-tritylisoindoline-6-boric acid and 8 mg of bis(triphenylphosphin)paradium (II) chloride, and thereafter, under an argon atmosphere, the resulting mixture was heated under reflux for 4 hours. Ethyl acetate was added to the reaction solution and the resulting organic layer was separated and rinsed with water, and thereafter, dried over anhydrous sodium sulfate and the solvent was distilled off under reduced pressure. The resulting residue was purified by silica gel column chromatography (eluent; chloroform:ethyl acetate=6:1) to obtain 71.7 mg of ethyl 1-cyclopropyl-9-methyl-8-(4-methoxy-2-tritylisoindoline-6-yl)-4-oxo-4H-quinolizine-3-carboxylate (I).

$^1$H-NMR(CDCl$_3$) δ: 0.75–0.79(2H, m), 0.99–1.04(2H, m), 1.43(3H, t, J=7.1 Hz), 2.34(1H, m), 3.79(3H, s), 4.04 (3H, s), 4.42(4H, q,J=7.1 Hz), 6.57(1H, s), 6.69 (1H, s), 7.02(1H, d, J=7.6 Hz), 7.15–7.62(15H, m), 8.39(1H, s), 9.43(1H, d, J=7.6 Hz)

Example 18

2 ml of THF, 0.7 ml ethanol, and 0.35 ml of 1N hydrochloric acid were added to 71.7 mg of ethyl 1-cyclopropyl-9-methyl-8-(4-methoxy-2-tritylisoindoline-6-yl)-4-oxo-4H-quinolizine-3-carboxylate (I), which was stirred at 50° C. for 2 hours. The solvent was distilled off under reduced pressure and water was added to the resulting residue, and the resulting residue was washed with ethyl acetate, and thereafter, the resulting water layer was concentrated under reduced pressure. 2 ml of methanol and 0.5 ml of 1N sodium hydroxide were added to the resulting residue and the resulting mixture was stirred at 50° C. for 2 hours. The reaction solution was concentrated under reduced pressure, and thereafter, dissolved in 10 ml of water and neutralized with 1N hydrochloric acid. The precipitated crystal was separated by filtering to obtain 25 mg of 1-cyclopropyl-9-methyl-8-(4-methoxy-isoindoline-6-yl)-4-oxo-4H-quinolizine-3-carboxylic acid (I).

$^1$H-NMR(CF$_3$COOD) δ: 1.16–1.17(2H, m), 1.50–1.52 (2H, m), 2.78(1H, m), 3.26(3H, s), 4.10(3H, s), 5.07(4H, m), 7.14(1H, s), 7.21(1H, s), 8.02(1H, d, J=6.3 Hz), 8.37(1H, brs), 8.83(1H, s), 9.55(1H, d, J=7.6 Hz)

FAB–MS m/z: 391(M+H)$^+$

Reference Example 50
(See Reaction Scheme 1)

27.26 g of 3-difluoromethyl-2-methylpyridine (XVI) was dissolved in 700 ml of anhydrous dichloromethane, and under cooling with ice, to which 45.19 g of 3-chloroperbenzoic acid was added, and the resulting mixture was stirred at 5° C. for 12 hours. The resulting organic layer was washed with 5% sodium carbonate solution, and thereafter, dried over anhydrous sodium sulfate, and the solvent was distilled off under reduced pressure. The resulting residue was purified by silica gel column chromatography (eluent; chloroform:methanol=9:1) to obtain 29.82 g of 3-difluoromethyl-2-methylpyridine N-oxide (XVII).

$^1$H-NMR(CDCl$_3$) δ: 2.60(3H, s), 6.77(1H, t, J=54.7 Hz), 7.25(1H, t, J=7.1 Hz), 7.42(1H, d, J=8.1 Hz), 8.37(1H, d, J=6.6 Hz)

Reference Example 51

31.38 g of 3-difluoromethyl-2-methylpyridine N-oxide (XVII) was dissolved in 64 ml of concentrated sulfuric acid, to which a mixed solution of 93 ml of concentrated sulfuric acid and 107 ml of 65% nitric acid were added, and the resulting mixture was heated at 95° C. for 20 hours. The reaction solution was poured into iced water and the precipitated crystal was separated by filtering to obtain 17.79 g of 3-difluoromethyl-2-methyl-4-nitropyridine N-oxide (XVIII).

$^1$H-NMR(CDCl$_3$) δ: 2.73(3H, s), 7.35(1H, t, J=52.5 Hz), 7.82(1H, d, J=7.3 Hz), 8.38(1H, d, J=7.3 Hz)

EI–MS m/z: 204(M$^+$)

Reference Example 52

0.52 g of 3-difluoromethyl-2-methyl-4-nitropyridine N-oxide (XVIII) was dissolved in 10 ml of concentrated hydrochloric acid, and in a closed tube, the resulting mixture was heated at 160° C. for 9 hours. The solvent was removed under reduced pressure, and thereafter, the resulting residue was purified by silica gel column chromatography (eluent; chloroform:methanol=19:1) to obtain 0.36 g of 4-chloro-3-difluoromethyl-2-methylpyridine N-oxide (VI).

$^1$H-NMR(CDCl$_3$) δ: 2.70(3H, s), 7.16(1H, t, J=53.7 Hz), 7.22(1H, d, J=7.1 Hz), 8.26(1H, d, J=7.1 Hz)

Reference Example 53

70 ml of acetic anhydride was added to 7.61 g of 4-chloro-3-difluoromethyl-2-methylpyridine N-oxide (VI), which was heated at 110° C. for 1 hour. The solvent was distilled off under reduced pressure, and thereafter, saturated aqueous sodium bicarbonate solution was added thereto and the resulting mixture was extracted with ether. The resulting organic layer was washed with saturated salt water, and thereafter, dried over anhydrous sodium sulfate and the solvent was distilled off under reduced pressure. The resulting residue was dissolved in 90% ethanol and 2.36 g of sodium hydroxide was added thereto and the resulting mixture was heated at 80° C. for 2 hours. The solvent was distilled off under reduced pressure, and thereafter, water was added thereto and the resulting mixture was extracted with chloroform. The resulting organic layer was washed with saturated salt water, and thereafter, dried over anhydrous sodium sulfate and the solvent was distilled off under reduced pressure. The resulting residue was purified by silica gel column chromatography (eluent; chlorohorm) to obtain 1.55 g of 4-chloro-3-difluoromethyl-2-hydroxymethylpyridine (VII).

$^1$H-NMR(CDCl$_3$) δ: 4.48(1H, brs), 4.98(2H, s), 7.19(1H, t, J=53.2 Hz), 7.33(1H, d, J=5.4 Hz), 8.54(1H, d, J=5.4 Hz)

Reference Example 54

0.91 ml of oxalyl chloride was dissolved in 20 ml of anhydrous dichloromethane, and under cooling at −78° C., 8 ml of anhydrous dichloromethane solution of 0.80 ml of anhydrous dimethylsulfoxide was dropped thereto. The resulting mixture was stirred at −78° C. for 40 minutes, and thereafter, 1.55 g of 4-chloro-3-difluoromethyl-2-hydroxymethylpyridine (VII) in 20 ml of anhydrous dichloromethane solution was dropped thereto. The resulting mixture was stirred at −78° C. for 30 minutes, and thereafter, the reaction temperature was elevated to −45° C., and the resulting mixture was stirred at the same temperature for 1 hour, and thereafter, 5.60 ml of triethylamine was dropped thereto and the temperature of the resulting mixture was elevated to a room temperature. Water was added to the resulting mixture, and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; chloroform) to obtain 1.36 g (4-chloro-3-difluoromethylpyridine)-2-carbardehyde (VIII).

$^1$H-NMR(CDCl$_3$) δ: 7.63(1H, d, J=5.4 Hz), 7.76(1H, t, J=53.0 Hz), 8.77(1H, d, J=5.4 Hz), 10.19(1H, s)

Reference Example 55

10 ml of THF solution of 1.36 g of (4-chloro-3-difluoromethylpyridine)-2-carbardehyde (VIII) was dropped to 13 ml of THF solution of magnesium cyclopropyl bromide which was prepared from 0.85 ml of cyclopropyl bromide and 0.26 g of magnesium. The resulting mixture was stirred at a room temperature for 2 hours, and poured into saturated ammonium chloride and extracted with chloroform. The resulting organic layer was washed with saturated salt water and dried over anhydrous sodium sulfate and the solvent was distilled off under reduced pressure. The resulting residue was purified by silica gel column chromatography (eluent; chloroform:ethyl acetate=60:1) to obtain 0.48 g of (4-chloro-3-difluoromethyl-2-pyridyl)cyclopropylmethane-1-ol (IX).

$^1$H-NMR(CDCl$_3$) δ: 0.43–0.60(4H, m), 1.20–1.28(1H, m), 3.75(1H, m), 4.91(1H, brs) 7.24(1H, t, J=53.2 Hz), 7.34(1H, d, J=5.1 Hz), 8.55(1H, d, J=5.1 Hz)

Reference Example 56

0.30 ml of oxalyl chloride was dissolved in 10 ml of anhydrous dichloromethane, and under cooling at −78° C., 0.27 ml of anhydrous dimethylsulfoxide in 3 ml of anhydrous dichloromethane solution was dropped thereto. The resulting mixture was stirred at −78° C. for 40 minutes, and thereafter, 0.62 g of (4-chloro-3-difluoromethyl-2-pyridyl)cyclopropylmethane-1-ol (IX) in 7 ml of anhydrous dichloromethane solution was dropped thereto. The resulting mixture was stirred at −78° C. for 30 minutes, and thereafter, the reaction temperature was elevated to −45° C. and the resulting mixture was stirred at the same temperature for 1 hour, and thereafter, 1.86 ml of triethylamine was dropped and the temperature of the resulting mixture was elevated to a room temperature. Water was added thereto and the resulting mixture was extracted with chloroform, and the resulting organic layer was washed with water and saturated salt water, and thereafter, dried over anhydrous sodium sulfate and the solvent was distilled off under reduced pressure. The resulting residue was purified by silica gel column chromatography (eluent; chloroform:ethyl acetate=19:1) to obtain 0.53 g of (4-chloro-3-difloromethyl-2-pyridyl)cyclopropylketone (X).

$^1$H-NMR(CDCl$_3$) δ: 1.16–1.35(4H, m), 2.91–2.98(1H, m), 7.25(1H, t, J=53.2 Hz), 7.54(1H, d, J=5.1 Hz), 8.63(1H, d, J=5.1 Hz)

Reference Example 57

0.82 g of (methoxymethyl) triphenyl phosphonium chloride was suspended in 8 ml of anhydrous ether, to which was dropped 2.71 ml of 0.88 M phenyllithium and the resulting mixture was stirred at a room temperature for 15 minutes. 6 ml of ether solution of 0.53 g of (4-chloro-3-difluoromethyl-2-pyridyl)cyclopropylketone (X) was dropped thereto and the resulting mixture was stirred at a room temperature for 2 hours. The resulting residue was separated by filtering and washed with ether, and thereafter, the ether filtrate and ether used for washing were collected together and the collected solution was washed with water, and thereafter, dried over anhydrous sodium sulfate and the solvent was distilled off under reduced pressure. The resulting residue was purified by silica gel column chromatography (eluent; hexane:ethyl acetate=4:1) to obtain 0.11 g of 2-(4-chloro-3-difluoromethyl-2-pyridyl)-2-cydopropyl-1-methoxyethene (XI).

$^1$H-NMR(CDCl$_3$)

δ1: 0.36–0.41(2H, m), 0.70–0.77(2H, m), 1.95–2.02(1H, m), 3.74(3H, s), 6.13(1H, d, J=0.7 Hz), 6.97(1H, t, J=53.2 Hz), 7.30(1H, d, J=5.4 Hz), 8.50(1H, d, J=5.4 Hz)

δ2: 0.37–0.41(2H, m), 0.61–0.66(2H, m), 1.64–1.71(1H, m), 3.57(3H, s), 6.23(1H, d, J=1.2 Hz), 6.74(1H, t, J=53.2 Hz), 7.30(1H, d, J=5.4 Hz), 8.57(1H, d, J=5.4 Hz)

Reference Example 58

130 mg of 2-(4-chloro-3-difluoromethyl-2-pyridyl)-2-cyclopropyl-1-methoxyethene (XI) was dissolved in 10 ml of THF, which was added 3 ml of dilute sulfuric acid and concentrated at 50° C. under reduced pressure. The resulting mixture was poured into water and neutralized with saturated sodium bicarbonate solution, and thereafter, extracted with chloroform. The resulting organic layer was washed with saturated salt water, and thereafter, dried over anhydrous sodium sulfate and the solvent was distilled off under reduced pressure. The resulting residue was purified by silica gel column chromatography (eluent; hexane:ethyl acetate=4:1) to obtain 70 mg of 2-(4-chloro-3-difluoromethyl-2-pyridyl)-2-cyclopropylethanal (XII).

$^1$H-NMR(CDCl$_3$) δ: 0.31–0.38(1H, m), 0.47–0.56(2H, m), 0.76–0.83(1H, m), 1.59–1.68(1H, m), 3.45(1H, d, J=9.8 Hz), 7.26(1H, t, J=53.2 Hz), 7.31(1H, d, J=5.1 Hz), 8.62(1H, d, J=5.1 Hz), 9.89(1H, d, J=1.7 Hz)

Reference Example 59

71.6 mg of 2-(4-chloro-3-difluoromethyl-2-pyridyl)-2-cyclopropylethanal (XII) was dissolved in 3 ml of anhydrous ethanol, to which were added 80 μl of piperidine, 80 μl of acetic acid and 220 μl of diethyl malonate and the resulting mixture was heated at 100° C. for 5 hours. The solvent was distilled off by under reduced pressure, and thereafter, the resulting mixture was diluted with ether, and the resulting organic layer was washed with water and saturated salt water, and dried over anhydrous sodium sulfate, and the solvent was distilled off by under reduced pressure. 2 ml of Dowtherm A was added to the resulting residue, and the resulting mixture was heated at 240° C. for 30 minutes. The reaction solution was purified directly by silica gel column chromatography (eluent; hexane→hexane:ethyl acetate= 1:1) to obtain 51.3 mg of ethyl 8-chloro-1-cyclopropyl-9-difluoromethyl-4-oxo-4H-quinolidine-3-carboxylate (XIII).

$^1$H-NMR(CDCl$_3$) δ: 0.68–0.72(2H, m), 1.13–1.18(2H, m), 1.42(3H, t, J=7.1 Hz), 2.10–2.20 (1H, m), 4.42(2H, q, J=7.1 Hz), 7.10(1H, d, J=7.8 Hz), 7.92(1H, t, J=52.2 Hz) 8.43(1H, s), 9.38(1H, d, J=7.8 Hz)

EI-MS m/z: 341(M$^+$)

Example 19

(See Reaction Scheme 2)

51 mg of ethyl 8-chloro-1-cyclopropyl-9-difluoromethyl-4-oxo-4H-quinolizine-3-carboxylate (XIII) was suspended in 0.5 ml of toluene, and 0.25 ml of ethanol, 0.12 ml of 2M aqueous sodium carbonate solution, 84 mg of 2-tritylisoindoline-5-boric acid and 5 mg of bis (triphenylphosphin)paradium (II) chloride, and thereafter, under an argon atmosphere, the resulting mixture was heated under reflux for 1.5 hours. Ethyl acetate was added to the reaction solution and the resulting organic layer was separated and washed with water, and thereafter, dried over anhydrous sodium sulfate and the solvent was distilled off under reduced pressure. The resulting residue was purified by silica gel column chromatography (eluent; chloroform-:ethyl acetate=8:1) to quantitatively obtain ethyl 1-cyclopropyl-9-difluoromethyl-8-(2-tritylisoindoline-5-yl)-4-oxo-4H-quinolizine-3-carboxylate (I).

Example 20

3 ml of THF, 1 ml of ethanol, and 0.5 ml of 1N hydrochloric acid were added to 99 mg of ethyl 1-cyclopropyl-9-difluoromethyl-8-(2-tritylisoindoline-5-yl)-4-oxo-4H-quinolizine-3-carboxylate (I), which was stirred at 50° C. for 2 hours. The solvent was distilled off under reduced pressure and water was added to the resulting residue, and the resulting residue was washed with ethyl acetate, and thereafter, the resulting water layer was concentrated under reduced pressure to quantitatively obtain ethyl 1-cyclopropyl-9-difluoromethyl-8-(isoindoline-5-yl)-4-oxo-4H-quinolizine-3-carboxylate (I).

FAB-MS m/z: 425(M+H)$^+$

Prescription Example will be represented as follows. However, the scope of the present invention should not be construed to be limited by Prescription Example.

Prescription Example 1

A tablet was prepared from the following components by a conventional procedure.

| Component | amount |
|---|---|
| Present compound | 100 mg |
| Cornstarch | 50 mg |
| Carboxymethyl cellulose calcium | 25 mg |
| Crystalline cellulose | 20 mg |
| Magnesium stearate | 5 mg |
| Total | 200 mg |

The in vitro antibacterial activity of the present compound (Example 2, 4, 6, 8, 10, 12, 14, 16 and 18) was tested by the standard method of Japan Chemical Therapy Institute using agar plate dilution method which is described in CHEMOTHERAPY Vol.29, 76–70, 1981. For an anaerobic bacteria, it was tested by the method described in CHEMOTHERAPY Vol. 27, 559–590, 1979. The minimum concentration at which the growth of a bacteria could be inhibited by the present compound was decided as MIC (μg/ml). The results are shown in Tables 1 and 2 below.

TABLE 1

Antibacterial spectrum MIC (μg/ml)

| | EXAMPLE 2 | EXAMPLE 4 | EXAMPLE 6 | LVFX* |
|---|---|---|---|---|
| Streptococcus aureus JCM2874 | 0.008 | 0.063 | 0.008 | 0.25 |
| Streptococcus aureus Clin-211 | 0.25 | 1 | 0.125 | 4 |
| Streptococcus Pneumoniae IID553 | 0.063 | 0.25 | 0.031 | 1 |
| Escherichia coli IFO 12734 | 0.031 | 0.125 | 0.016 | 0.063 |
| Pseudomonas aeruginosa CSJ 1853 | 0.25 | 1 | 0.25 | 0.5 |
| Bacteroides fragilis GAI0675 | 0.031 | 0.25 | 0.031 | 0.5 |

*levofloxacin

TABLE 2

Antibacterial spectrum MIC (μg/ml)

| | Example 8 | Example 10 | Example 12 | Example 14 | Example 16 | Example 18 |
|---|---|---|---|---|---|---|
| Streptococcus Aureus JCM2874 | 0.063 | 0.063 | 0.031 | 0.008 | 0.125 | 0.031 |

TABLE 2-continued

Antibacterial spectrum MIC (μg/ml)

| | Example 8 | Example 10 | Example 12 | Example 14 | Example 16 | Example 18 |
|---|---|---|---|---|---|---|
| Streptococcus Aureus Clin-211 | 0.5 | 1 | 1 | 0.125 | 2 | 0.5 |
| Streptococcus Pneumoniae IID553 | 0.25 | 0.25 | 0.25 | 0.031 | 0.5 | 0.125 |
| Escherichia Coli IFO12734 | 0.063 | 0.125 | 0.125 | 0.031 | 0.5 | 0.125 |
| Pseudomonas Aeruginosa CSJ1853 | 1 | 4 | 4 | 0.5 | 8 | 2 |
| Bacteroides GMI0675 | 0.25 | 0.5 | 0.25 | 0.016 | 0.25 | 0.063 |

The present invention provides a novel synthetic 4-oxoquinolizine antimicrobial agent which exhibits a strong antibacterial activity against Gram-positive, Gram-negative bacteria or anaerobic bacteria.

What is claimed is:

1. A compound represented by the following Formula (I) or a pharmaceutically acceptable salt thereof:

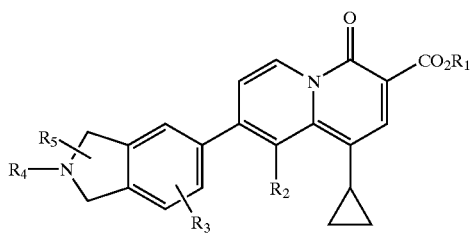

wherein
   $R_1$ represents a hydrogen atom or a carboxyl-protecting group,
   $R_2$ represents a hydrogen atom, a halogen atom, a lower alkyl group, a lower alkoxy group or a hydroxyl group,
   $R_3$ represents a hydrogen atom, a halogen atom, a lower alkyl group, a lower alkoxy group, a lower alkylthio group, a nitro group, a cyano group, a hydroxyl group or an amino group;
   $R_4$ represents a hydrogen atom, an amino-protecting group, an alkyl group or a cycloalkyl group, and
   $R_5$ represents a hydrogen atom, a halogen atom, an alkyl group, an alkenyl group, a cycloalkyl group, an aryl group, an alkoxy group, an alkylthio group, a hydroxyl group, an imino group or an amino group.

2. The compound or the pharmaceutically acceptable salt thereof of claim 1, wherein in Formula (I), $R^2$ is a lower alkyl group or a lower alkoxy group.

3. The compound or the pharmaceutically acceptable salt thereof of claim 1, wherein in Formula (I), $R^3$ is a hydrogen atom or a lower alkoxy group.

4. The compound or the pharmaceutically acceptable salt thereof of claim 1, wherein in Formula (I), $R^5$ is a hydrogen atom or a lower alkyl group.

5. The compound or the pharmaceutically acceptable salt thereof of claim 1, wherein in Formula (I), $R^1$ is a hydrogen atom.

6. An antimicrobial agent comprising the compound of claim 1 or a pharmaceutically acceptable salt thereof as an effective component.

7. The antimicrobial agent of claim 6 against a Gram-positive bacterium.

8. The antimicrobial agent of claim 7, wherein said Gram-positive bacterium is Streptococcus aureus or Streptococcus pneumoniae.

9. The antimicrobial agent of claim 6 against a Gram-negative bacterium.

10. The antimicrobial agent of claim 9, wherein said Gram-negative bacterium is Escherichia coli or Pseudomonas aeruginosa.

11. The antimicrobial agent of claim 6 against an anaerobic bacterium.

12. The antimicrobial of claim 11, wherein the anaerobic bacterium is Bacteriodes fragilis.

13. A method of preparing the compound of claim 1, comprising reacting a compound represented by the following Formula (I):

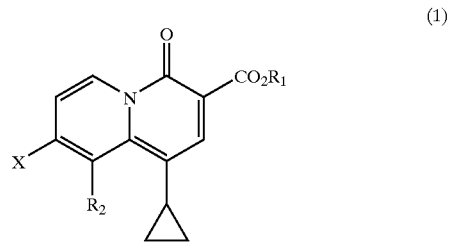

wherein
   $R_1$ represents a hydrogen atom or a carboxyl-protecting group,
   $R_2$ represents a hydrogen atom, a halogen atom, a lower alkyl group, a lower alkoxy group or a hydroxyl group; and
   X represents a halogen atom, with a compound represented by the following Formula (3),

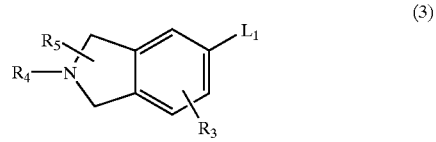

wherein
   $R_3$ represents a hydrogen atom, a halogen atom, a lower alkyl group, a lower alkoxy group, a lower alkylthio group, a nitro group, a cyano group, a hydroxyl group, or an amino group, R$_4$ represents a hydrogen atom, an amino-protecting group, an alkyl group or a cycloalkyl group, R$_5$ represents a hydrogen atom, a halogen atom, an alkyl group, an alkenyl group, a cycloalkyl group, an aryl group, an alkoxy group, an alkylthio group, a hydroxyl group, an imino group, or an amino group, and L$_1$ represents tin(an alkyl group)$_3$ or boron(a lower alkoxy group)$_2$.

14. A method of preparing the compound of claim 1, comprising reacting a compound represented by the following Formula (2):

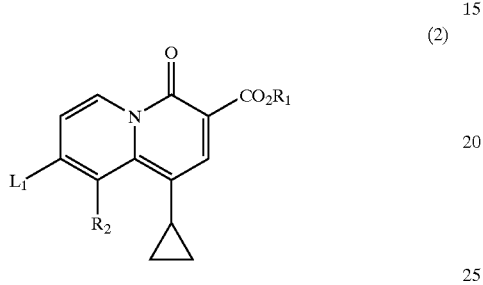

wherein

R$_1$ represents a hydrogen atom or a carboxyl-protecting group,

R$_2$ represents a hydrogen atom, a halogen atom, a lower alkyl group, a lower alkoxy group or a hydroxyl group, and L$_1$ represents tin(an alkyl group)$_3$ or boron(an lower alkoxy group)$_2$, with a compound represented by the following Formula (4)

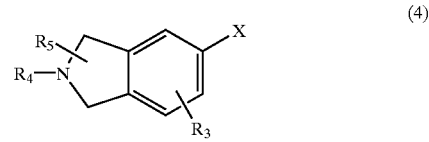

wherein

R$_3$ represents a hydrogen atom, a halogen atom, a lower alkyl group, a lower alkoxy group, a lower alkylthio group, a nitro group, a cyano group, a hydroxyl group, or an amino group, R$_4$ represents a hydrogen atom, an amino-protecting group, an alkyl group or a cycloalkyl group, R$_5$ represents a hydrogen atom, a halogen atom, an alkyl group, an alkenyl group, a cycloalkyl group, an aryl group, an alkoxy group, an alkylthio group, a hydroxyl group, an imino group, or an amino group, and X represents a halogen atom.

* * * * *